United States Patent
Okihara

(10) Patent No.: US 11,998,722 B2
(45) Date of Patent: Jun. 4, 2024

(54) FEMALE SYRINGE BARREL, SYRINGE KIT, AND SYRINGE CONNECTION METHOD

(71) Applicant: TERUMO KABUSHIKI KAISHA, Tokyo (JP)

(72) Inventor: Hitoshi Okihara, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1066 days.

(21) Appl. No.: 16/846,801

(22) Filed: Apr. 13, 2020

(65) Prior Publication Data

US 2020/0238013 A1 Jul. 30, 2020

Related U.S. Application Data

(63) Continuation of application No. PCT/JP2017/037181, filed on Oct. 13, 2017.

(51) Int. Cl.
*A61M 5/31* (2006.01)
*A61M 5/00* (2006.01)
(Continued)

(52) U.S. Cl.
CPC .......... *A61M 5/3134* (2013.01); *A61M 5/002* (2013.01); *A61M 5/31596* (2013.01);
(Continued)

(58) Field of Classification Search
CPC .. A61M 2039/1077; A61M 2039/1094; A61M 2039/1011; A61M 2039/1033;
(Continued)

(56) References Cited

U.S. PATENT DOCUMENTS 6,610,034 B1 * 8/2003 Fischer ............... A61C 5/68
604/235
8,226,598 B2 * 7/2012 Dunn .................. A61J 1/2089
604/82
(Continued)

FOREIGN PATENT DOCUMENTS

EP 0 805 930 B1 6/2002
JP 2013520287 A 6/2013
(Continued)

OTHER PUBLICATIONS

Office Action (The First Office Action) dated Nov. 3, 2022, by the State Intellectual Property Office of People's Republic of China in corresponding Chinese Patent Application No. 201780095737.8 and an English Translation of the Office Action. (15 pages).
(Continued)

*Primary Examiner* — Kevin C Sirmons
*Assistant Examiner* — Alexandra Lalonde
(74) *Attorney, Agent, or Firm* — BUCHANAN INGERSOLL & ROONEY PC

(57) ABSTRACT

A female syringe barrel is disclosed, which includes two protrusions provided on a cylindrical portion. A length (Lp) of each protrusion of the two protrusions along a direction, perpendicular to an axis of the cylindrical portion and perpendicular to a direction in which each protrusion of the two protrusions protrudes from the cylindrical portion, is 2.0 mm to 4.5 mm. A width of each protrusion of the two protrusions along an axial direction of the cylindrical portion is 1.0 mm to 2.1 mm. Each protrusion of the two protrusions has an inclined surface, which opposes a trailing flank of a screw when the two protrusions are engaged into the screw of a lock adapter, in an end portion close to a barrel body.

18 Claims, 15 Drawing Sheets

(51) Int. Cl.
*A61M 5/315* (2006.01)
*A61M 39/10* (2006.01)

(52) U.S. Cl.
CPC . *A61M 39/1011* (2013.01); *A61M 2005/3131* (2013.01); *A61M 2039/1077* (2013.01)

(58) Field of Classification Search
CPC .... A61M 5/178; A61M 5/3134; A61M 5/002; A61M 5/31596; A61M 2005/3131; A61M 39/1011; A61M 39/10; A61M 5/344; A61M 5/347; A61M 2039/0027; A61J 1/2096; A61J 1/2089; A61J 1/20; A61J 1/2048; A61J 7/0053; F16L 15/00; F16L 15/002; F16L 15/06; F16L 37/00; F16L 37/10; F16L 37/107; F16L 37/113; F16L 37/24; F16L 37/244; F16L 37/2445
See application file for complete search history.

(56) References Cited

U.S. PATENT DOCUMENTS

| | | | |
|---|---|---|---|
| 2007/0068594 A1* | 3/2007 | Fischer | A61J 1/2096 604/416 |
| 2008/0140020 A1 | 6/2008 | Shirley | |
| 2008/0140055 A1 | 6/2008 | Shirley | |
| 2008/0188816 A1* | 8/2008 | Shimazaki | A61M 5/34 604/240 |
| 2010/0324501 A1* | 12/2010 | Horiuchi | A61M 5/31513 604/222 |
| 2013/0072893 A1 | 3/2013 | Takemoto | |
| 2016/0184522 A1* | 6/2016 | Horiuchi | A61M 5/3129 604/199 |
| 2016/0206821 A1* | 7/2016 | Horiuchi | A61J 1/2096 |
| 2016/0354594 A1 | 12/2016 | Uehara et al. | |
| 2017/0014616 A1 | 1/2017 | Davis et al. | |

FOREIGN PATENT DOCUMENTS

| | | | | |
|---|---|---|---|---|
| JP | 2013132349 A | | 7/2013 | |
| WO | WO-2015151692 A1 * | | 10/2015 | A61M 5/3137 |

OTHER PUBLICATIONS

The extended European Search Report dated Sep. 14, 2020, by the European Patent Office in corresponding European Patent Application No. 17928323.9-1122. (9 pages).

International Search Report and Written Opinion issued in International Patent Application No. PCT/JP2017/037181, 8 pages (dated Nov. 21, 2017).

* cited by examiner

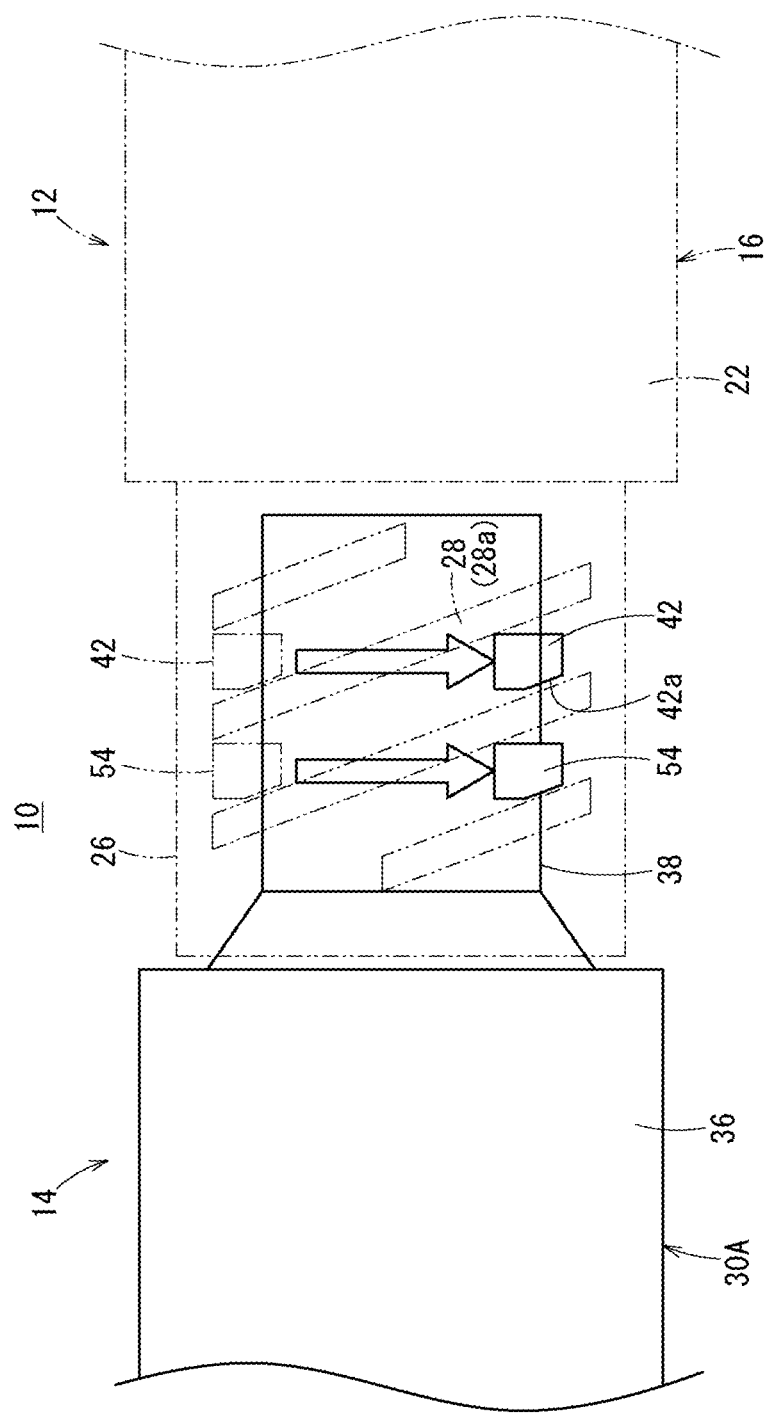

FEMALE SYRINGE BARREL, SYRINGE KIT, AND SYRINGE CONNECTION METHOD

CROSS-REFERENCES TO RELATED APPLICATIONS

This application is a continuation of International Application No. PCT/JP2017/037181 filed on Oct. 13, 2017, the entire content of which is incorporated herein by reference.

FIELD OF THE DISCLOSURE

The present disclosure relates to a female syringe barrel, a syringe kit, and a syringe connection method.

BACKGROUND DISCUSSION

A syringe kit for mixing two medicines, a first medicine in a first barrel and a second medicine in a second barrel is disclosed, for example, in JP 2013-132349 A. This syringe kit includes a first barrel (female syringe barrel) having a connecting tube portion provided with an inner tapered surface on an inner circumference and a male screw on an outer circumference, and a second barrel (male syringe barrel) having a nozzle portion, which has an outer tapered surface on an outer circumference and is connectable to the inner tapered surface on the inner circumference of the connecting tube portion, and a screw tube portion provided with a female screw, engageable with the male screw, on an inner circumference. In the syringe kit, the connecting tube portion of the first barrel and the screw tube portion of the second barrel are connected by screwing in order to mix a medicine in the first barrel and a medicine in the second barrel.

In the syringe kit of JP 2013-132349 A described above, a screwing portion of the connecting tube portion of the first barrel and a screwing portion of the screw tube portion of the second barrel are both screw-shaped, and thus, excessive screwing is possible. Therefore, there is a problem that the tapered surfaces excessively fit together, and the connecting tube portion (mouth) of the first barrel is damaged or deformed, the liquid tightness between the nozzle and the cylindrical portion can deteriorate. In addition, there is a problem that a distal end portion of either the first barrel or the second barrel is twisted and is damaged or deformed, the liquid tightness between the nozzle and the cylindrical portion may deteriorate.

SUMMARY

In accordance with an aspect, a female syringe barrel, a syringe kit, and a syringe connection method are disclosed, which are capable of preventing damage and deformation of a female syringe barrel or a male syringe barrel caused by an excessive torque and preventing deterioration in liquid tightness between a nozzle and a cylindrical portion when screwing the female syringe barrel and the male syringe barrel.

In accordance with an aspect, a female syringe barrel is disclosed, which includes: a hollow barrel body having an inner circumferential surface on which a gasket is slidable; and a cylindrical portion that protrudes in a distal end direction from a distal end of the barrel body and is configured as a female luer to which a nozzle of a male syringe is connectable. The cylindrical portion has two protrusions which are provided on opposite sides on an outer circumferential portion of the cylindrical portion and engageable with a screw provided on a lock adapter of the male syringe. A length of the protrusion along a direction, perpendicular to an axis of the cylindrical portion and perpendicular to a direction in which the protrusion protrudes from the cylindrical portion, is 2.0 mm to 4.5 mm. A width of the protrusion along an axial direction of the cylindrical portion is 1.0 mm to 2.1 mm. Each of the two protrusions has an inclined surface, which opposes a trailing flank of the screw of the lock adapter when the two protrusions are engaged (i.e., screwed) with the screw of the lock adapter, in an end portion close to the barrel body.

According to the female syringe barrel of the present disclosure adopting the above configuration, the protrusion advances over a screw thread of the lock adapter when an excessive torque is applied at the time of screwing the protrusion and the screw of the lock adapter. For this reason, excessive tightening can be prevented, damage and deformation of the cylindrical portion of the female syringe barrel can be prevented, and deterioration in liquid tightness between the nozzle and the cylindrical portion can be prevented.

In the above female syringe barrel, the cylindrical portion may have a ring-shaped protruding portion that protrudes outward from a distal end portion of the cylindrical portion, and the two protrusions may be formed on an outer circumferential portion of the ring-shaped protruding portion.

With this configuration, when the protrusion advances over the screw thread of the lock adapter, the protrusion and the cylindrical portion are less likely to be deformed, and the liquid tightness between the nozzle and the cylindrical portion can be kept favorable.

In the above female syringe barrel, a distal end protruding portion protruding from the distal end portion of the cylindrical portion toward a distal end may be provided, and the distal end protruding portion may be located to be closer to the distal end than the two protrusions.

With this configuration, when the protrusion advances over the screw thread of the lock adapter, the protrusion and the cylindrical portion are less likely to be deformed, and the liquid tightness between the nozzle and the cylindrical portion is kept favorable.

In the above female syringe barrel, the female syringe barrel may be made of a cyclic polyolefin.

Since the cyclic polyolefin has high rigidity and toughness, when the protrusion advances over the screw thread of the lock adapter, the protrusion and the cylindrical portion are less likely to be deformed, and the liquid tightness between the nozzle and the cylindrical portion is kept favorable.

In the above female syringe barrel, an outer diameter of the barrel body may be 6.7 mm or larger, and an axial length of the barrel body may be 35 mm or longer.

In general, in the case of a barrel for a syringe, provided with a barrel body having the above external dimensions, screwing is performed by gripping the barrel body, and thus, the screwing can be reliably performed, but it is easy to apply a strong torque so that it is easy to cause breakage or deformation. According to the present disclosure, however, even if the barrel body has external dimensions that enables easy gripping, it is possible to prevent the damage and deformation of the cylindrical portion as described above, and the deterioration in liquid tightness between the nozzle and the cylindrical portion can be effectively prevented. Therefore, the present disclosure is particularly advantageous when the barrel body has the external dimensions that enable rather easy gripping.

In the above female syringe barrel, the cylindrical portion may have a proximal-end-side protruding portion that protrudes from the outer circumferential portion of the cylindrical portion and is provided at a position closer to a proximal end than the protrusion, and the proximal-end-side protruding portion may abut on an inner circumferential surface of the lock adapter so as to suppress an inclination of the axis of the cylindrical portion with respect to an axis of the lock adapter when the two protrusions of the cylindrical portion are engaged with the screw of the lock adapter of the male syringe.

With this configuration, the inclination of the axis is suppressed by the proximal-end-side protruding portion when the two protrusions of the cylindrical portion are engaged with the screw of the lock adapter of the male syringe, and thus, it is possible to prevent the breakage of the cylindrical portion due to uneven stress in the circumferential direction.

In the above female syringe barrel, the cylindrical portion may have an abutment portion having an outer diameter of 6.4 to 6.8 mm on the outer circumferential portion of the cylindrical portion, the abutment portion is located to be closer to a proximal end than the two protrusions, and the abutment portion may abut on an inner circumferential surface of the screw of the lock adapter so as to suppress the inclination of the axis of the cylindrical portion with respect to the axis of the lock adapter when the two protrusions of the cylindrical portion are engaged with the screw of the lock adapter of the male syringe.

With this configuration, the inclination of the axis is suppressed by the abutment portion when the two protrusions of the cylindrical portion are engaged with the screw of the lock adapter of the male syringe, and thus, it is possible to prevent the breakage of the cylindrical portion due to uneven stress in the circumferential direction.

In the above female syringe barrel, the abutment portion may be provided continuously from proximal ends of the two protrusions to a position separated by at least 4 mm toward the female barrel body from a distal end of the cylindrical portion.

The above female syringe barrel may further include an outer cylinder that surrounds the outer circumferential portion of the cylindrical portion and is not rotatable with respect to the cylindrical portion, and the inclination of the axis of the cylindrical portion with respect to the axis of the lock adapter may be prevented as the lock adapter is inserted between the cylindrical portion and the outer cylinder, and an inner circumferential surface of the outer cylinder abuts on an outer circumferential surface of the lock adapter when the two protrusions of the cylindrical portion are engaged with the screw of the lock adapter of the male syringe.

With this configuration, the inclination of the axis is suppressed by the outer cylinder when the two protrusions of the cylindrical portion are engaged with the screw of the lock adapter of the male syringe, and thus, it is possible to prevent the breakage of the cylindrical portion due to uneven stress in the circumferential direction.

In the above female syringe barrel, the length of the protrusion may be 2.7 mm to 3.5 mm, the width of the protrusion may be 1.5 mm to 2.1 mm, and the protrusion may have a chamfered corner chamfered on a side surface opposing the inclined surface.

With this configuration, even when the protrusions are set in the above range, at the time of screwing the two protrusions of the cylindrical portion with the screw of the lock adapter of the male syringe, corners of the protrusions hardly interfere with the screw due to the chamfered corner, and it is possible to help prevent the occurrence of poor screwing.

In accordance with another aspect, a syringe kit is disclosed, which includes: a male syringe having a male syringe barrel that includes a nozzle configured as a male luer and a lock adapter provided with a screw; and a female syringe having a female syringe barrel that includes a cylindrical portion configured as a female luer to which the nozzle is connectable, two protrusions which protrude from an outer circumferential surface of the cylindrical portion and are engageable with the screw of the lock adapter, and a female barrel body connected to the cylindrical portion. When the screw and the two protrusions are engaged, the protrusions advance over a screw thread of the lock adapter by a torque smaller than a torque at which the female syringe breaks when the female syringe is engaged with a convex reference conical fitting for a stress crack test specified in ISO 594-2.

According to the syringe kit of the present disclosure adopting the above configuration, when the male syringe and the female syringe are connected by screwing, excessive tightening can be prevented, damage and deformation of the cylindrical portion of the female syringe can be prevented, and deterioration in liquid tightness between the nozzle and the cylindrical portion can be prevented.

In the above syringe kit, both the male syringe barrel and the female syringe barrel may be made of a cyclic polyolefin.

Since the cyclic polyolefin has a relatively high rigidity and toughness, when the protrusion advances over the screw thread of the lock adapter, the protrusion and the cylindrical portion are less likely to be deformed, and the nozzle is also less likely to be deformed, and thus, the liquid tightness between the nozzle and the cylindrical portion can be favorably kept.

In the above syringe kit, both of an outer diameter of the male barrel body and an outer diameter of the female barrel body may be 6.7 mm or larger, and both of an axial length of the male barrel body and an axial length of the female barrel body may be 35 mm or longer.

In general, a barrel for a syringe having a barrel body of such external dimensions is likely to be subjected to a strong torque during the screwing, and is likely to be broken or deformed. According to this disclosure, however, it is possible to prevent the damage and deformation of the cylindrical portion and to effectively prevent the deterioration in liquid tightness between the nozzle and the cylindrical portion, which is advantageous.

In the above syringe kit, an inner diameter of the screw of the lock adapter may be 6.8 mm to 7.2 mm, the cylindrical portion may have an abutment portion provided at a position closer to a proximal end than the two protrusions on the outer circumferential portion of the cylindrical portion, and the abutment portion may have an outer diameter of 6.4 mm to 6.8 mm. When the two protrusions of the cylindrical portion are engaged with the screw of the lock adapter of the male syringe, the abutment portion may abut on an inner circumferential surface of the screw of the lock adapter so as to suppress the inclination of the axis of the cylindrical portion with respect to the axis of the lock adapter.

With this configuration, the inclination of the axis is suppressed by the abutment portion when the two protrusions of the cylindrical portion are engaged with the screw of the lock adapter of the male syringe, and thus, it is possible to prevent the breakage of the cylindrical portion due to uneven stress in the circumferential direction.

In addition, the present disclosure provides a syringe connection method for connecting a male syringe and a female syringe by screwing. The male syringe has a male syringe barrel that includes a nozzle configured as a male luer, and a lock adapter provided with a screw. The female syringe has a female syringe barrel that includes a cylindrical portion configured as a female luer to which the nozzle is connected, and two protrusions engageable with the screw of the lock adapter. When the screw and the protrusions are engaged, the protrusions advance over a screw thread of the lock adapter by a predetermined torque, and a click feeling is generated along with the advancement.

As a result, it is possible to prevent the female syringe barrel or the male syringe barrel from being damaged or deformed due to an excessive torque during the screwing and to prevent deterioration in liquid tightness between the nozzle and the cylindrical portion, and a user who has performed the screwing operation can easily know that the screwing between the protrusions and the screw has been completed based on the generated click feeling.

In the above syringe connection method, the cylindrical portion may have an abutment portion provided at a position closer to a proximal end than the two protrusions on the outer circumferential portion of the cylindrical portion, and the abutment portion may abut on an inner circumferential surface of the lock adapter to suppress an inclination of an axis of the cylindrical portion with respect to an axis of the lock adapter when the screw and the two protrusions are engaged.

As a result, the inclination of the axis is suppressed by the abutment portion when the two protrusions of the cylindrical portion are engaged with the screw of the lock adapter of the male syringe, and thus, it is possible to prevent the breakage of the cylindrical portion due to uneven stress in the circumferential direction.

According to the female syringe barrel, the syringe kit, and the syringe connection method of the present disclosure, it is possible to prevent the female syringe barrel or the male syringe barrel from being damaged or deformed due to the excessive torque during the screwing, and to prevent the deterioration in liquid tightness between the nozzle and the cylindrical portion.

BRIEF DESCRIPTION OF THE DRAWINGS

FIG. 13 is a schematic view illustrating a state where a protrusion and a proximal-end-side protrusion of the female syringe barrel according to the second modification advance over screws of the male syringe.

DETAILED DESCRIPTION

Set forth below with reference to the accompanying drawings is a detailed description of embodiments of a female syringe barrel, a syringe kit, and a syringe connection method representing examples of the inventive female syringe barrel, the syringe kit, and the syringe connection method disclosed here.

Figure 1:
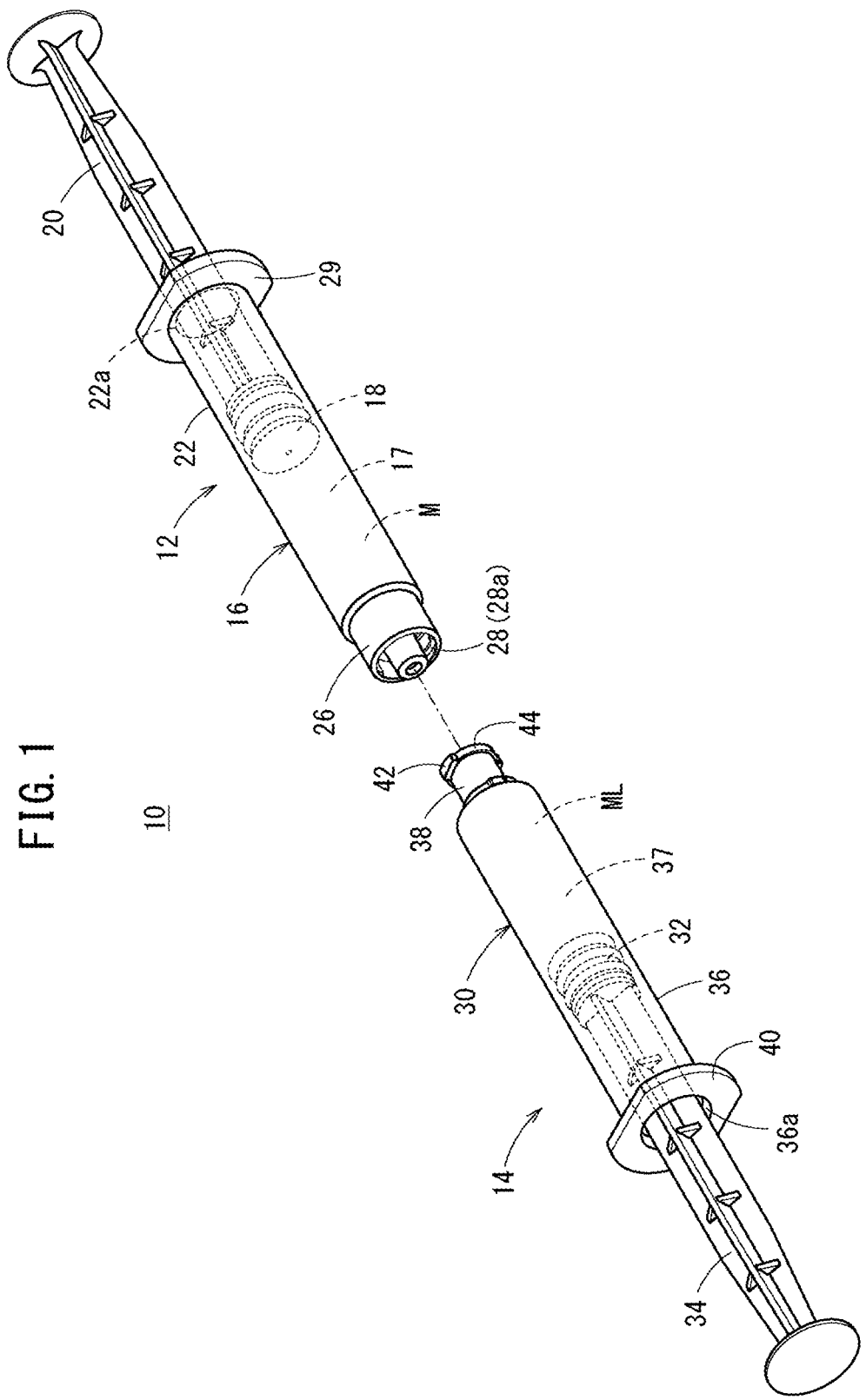
FIG. 1 is a perspective view of a syringe kit according to an embodiment disclosed here.

A syringe kit 10 according to the present embodiment illustrated in FIG. 1 is a mixing kit configured to mix a filling in one barrel and a filling in the other barrel. The syringe kit 10 includes a male syringe 12 and a female syringe 14 that can be screw-connected to each other. Both the male syringe 12 and the female syringe 14 are configured as prefilled syringes which are pre-filled with contents such as medicines.

Note that a side of the male syringe 12 that is connected to the female syringe 14 or a direction of the female syringe 14 is referred to as a "distal end portion" or a "distal end direction", and the opposite side or the opposite direction is referred to as a "proximal end portion" or a "proximal end direction" in the following description. In addition, a side of the female syringe 14 that is connected to the male syringe 12 or a direction of the male syringe 12 is referred to as a "distal end portion" or a "distal end direction", and the opposite side or the opposite direction is referred to as a "proximal end portion" or a "proximal end direction".

In accordance with an embodiment, the male syringe 12 includes: a male syringe barrel 16, which is a hollow body; a gasket 18 slidably inserted into the male syringe barrel 16; a pusher 20 connected to the gasket 18; and a medicine M filling a barrel chamber 17 formed by the male syringe barrel 16 and the gasket 18.

Figure 2:
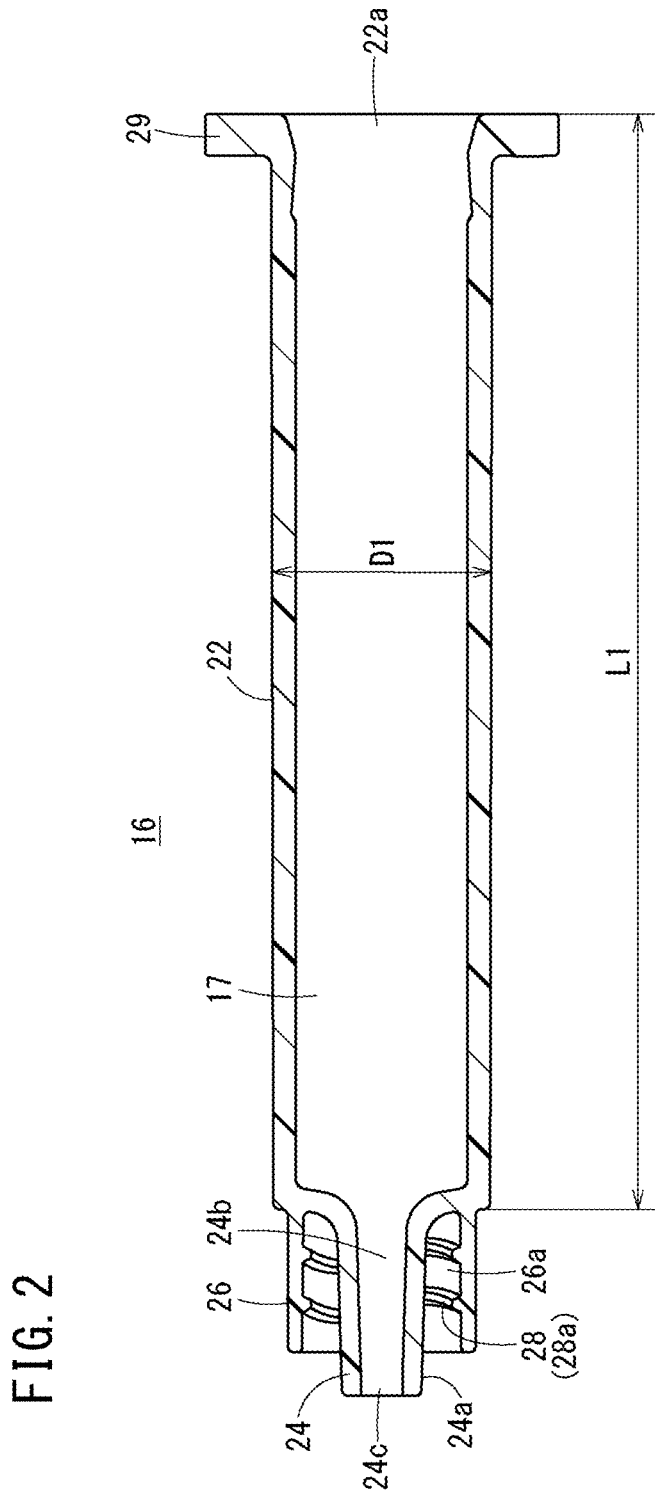
FIG. 2 is a cross-sectional view of a male syringe barrel.

As illustrated in FIG. 2, the male syringe barrel 16 can include: a barrel body 22 (male barrel body) having a substantially cylindrical shape and a proximal end opening 22a formed at a proximal end; a nozzle 24 provided at a distal end of the barrel body 22; a lock adapter 26 provided outside the nozzle 24; and a flange 29 formed to protrude radially outward from the proximal end of the barrel body 22. In accordance with an embodiment, the barrel body 22, the nozzle 24, the lock adapter 26, and the flange 29 can be integrally formed.

In accordance with an aspect, an outer diameter D1 of the barrel body 22 is not particularly limited, but is, for example, preferably 6.7 mm or larger. In addition, an axial length L1 of the barrel body 22 is not particularly limited, but is, for example, preferably 35 mm or longer, and more preferably 47 mm or longer. When the outer diameter D1 and the axial length L1 of the barrel body 22 are as disclosed herein, screwing can be rather easily performed by gripping the barrel body 22 at the time of connecting the male syringe 12 with the female syringe 14.

The nozzle 24 extends in the distal end direction while being reduced in diameter from the center of the distal end of the barrel body 22. The nozzle 24 has a passage 24b penetrating in the axial direction and communicating with an inner cavity (the barrel chamber 17) of the barrel body 22.

In accordance with an embodiment, the nozzle 24 has a circular cross-sectional outer shape and is configured as a male luer having a tapered outer circumferential surface 24a whose outer diameter decreases toward the distal end direction. The nozzle 24 can be connected to a cylindrical portion 38 (female luer), which will be described later, of the female syringe 14. The nozzle 24 protrudes in the distal end direction from a distal end surface of the lock adapter 26.

Note that a cap (not illustrated) can be mounted on the nozzle 24 in an initial state of the male syringe 12 illustrated in FIG. 1, and a distal end opening 24c of the nozzle 24 can be sealed by this cap. The cap is detached from the nozzle 24 at the time of using the male syringe 12 (at the time of using the syringe kit 10).

In FIG. 2, the lock adapter 26 is formed in a substantially hollow cylindrical shape that extends in the distal end direction from the distal end of the barrel body 22 and surrounds the nozzle 24 concentrically. An annular recess 26a that is open in the distal end direction is formed between an inner circumferential portion of the lock adapter 26 and an outer circumferential portion of the nozzle 24. A screw 28 is formed on an inner circumferential surface of the lock adapter 26. The screw 28 has a screw thread 28a protruding inward from the inner circumferential surface of the lock adapter 26.

In FIG. 1, the gasket 18 is inserted into the barrel body 22 via the proximal end opening 22a that is open at the proximal end of the barrel body 22. The proximal end side of the barrel body 22 is sealed by the gasket 18 in a liquid-tight manner. The gasket 18 can be made of an elastic material such as a rubber material. The gasket 18 has an outer circumferential portion being in liquid-tight contact with an inner circumferential surface of the barrel body 22 and is arranged to be slidable inside the barrel body 22.

The gasket 18 is connected to a distal end portion of the pusher 20. When a user presses the pusher 20 in the axial direction (distal end direction or proximal end direction), the gasket 18 slides in the axial direction inside the barrel body 22. Note that the pusher 20 may be connected to the gasket 18 at the time of using the male syringe 12.

In accordance with an aspect, the medicine M may be any medicine such as a powdered medicine, a lyophilized medicine, a solid medicine, and a liquid medicine as long as being dissolved, diluted, and mixed by a medical liquid ML (specifically, a dissolving solution such as a saline solution) filling the inside of the female syringe 14. Examples of the medicine M include protein preparations, peptide preparations, antitumor agents, vitamins (multivitamins), various amino acids, antithrombotic agents such as heparin, insulin, antibiotics, analgesics, cardiotonic agents, intravenous injection anesthetics, medical narcotics, anti-parkinsonian agents, ulcer treatment agents, corticosteroids, arrhythmic agents, and the like.

In accordance with an aspect, the female syringe 14 includes: a female syringe barrel 30, which is a hollow body; a gasket 32 slidably inserted into the female syringe barrel 30; a pusher 34 connected to the gasket 32; and the medical liquid ML filling a barrel chamber 37 formed by the female syringe barrel 30 and the gasket 32.

Figure 3:
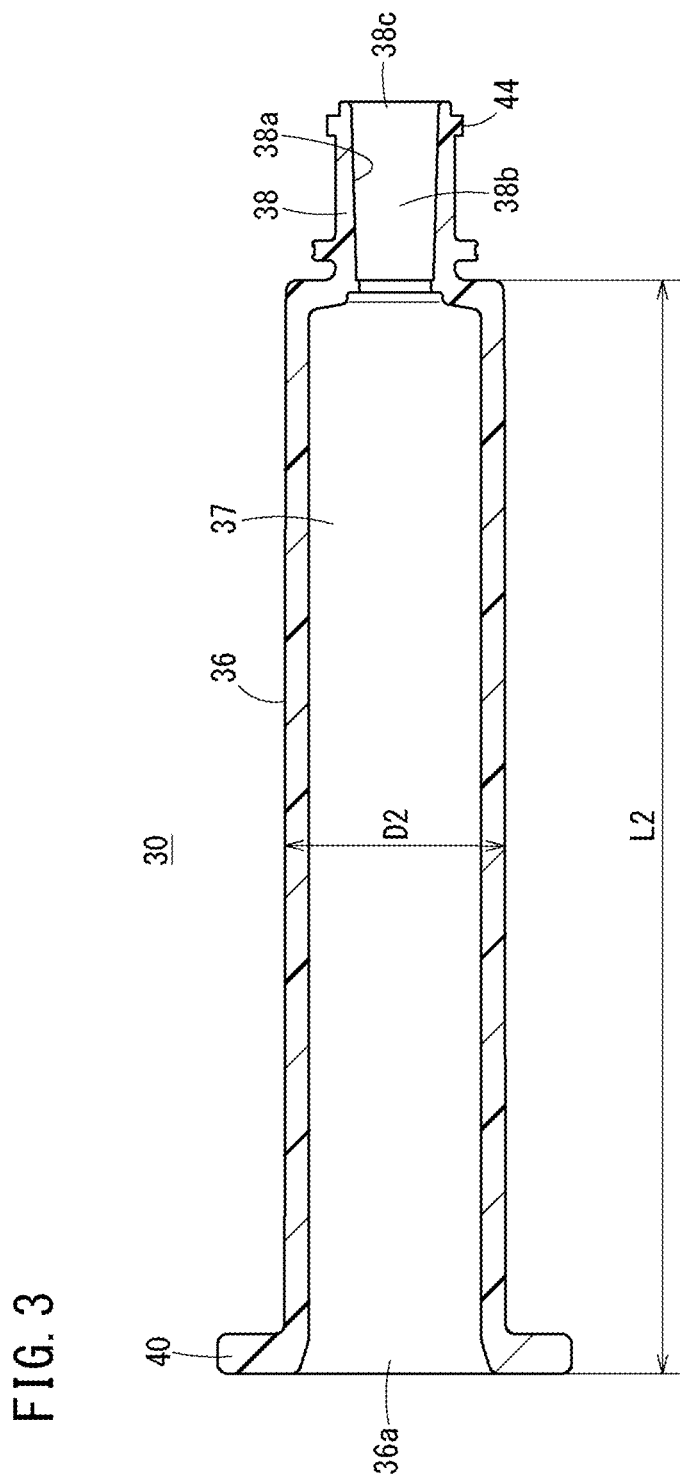
FIG. 3 is a cross-sectional view of a female syringe barrel.

As illustrated in FIG. 3, the female syringe barrel 30 has: a barrel body 36 (female barrel body) having a substantially cylindrical shape and a proximal end opening 36a formed at a proximal end; a cylindrical portion 38 protruding in the distal end direction from a distal end of the barrel body 36; and a flange 40 formed to protrude radially outward from the proximal end of the barrel body 36. The barrel body 36, the cylindrical portion 38, and the flange 40 can be integrally formed. Note that the cylindrical portion 38 can be thinner than the barrel body 36 in FIG. 3, but the cylindrical portion 38 may have the same thickness as the barrel body 36 or may be thicker than the barrel body 36.

An outer diameter D2 of the barrel body 36 is not particularly limited, but is preferably 6.7 mm or larger. In addition, an axial length L2 of the barrel body 36 is not particularly limited, but is preferably 35 mm or longer, and more preferably 47 mm or longer. When the outer diameter D2 and the axial length L2 of the barrel body 36 are as disclosed herein, screwing can be easily performed by gripping the barrel body 36 at the time of connecting the female syringe 14 with the male syringe 12.

The cylindrical portion 38 extends in the distal end direction from the center portion of the distal end of the barrel body 36. The cylindrical portion 38 has a passage 38b extending in the axial direction and communicating with an inner cavity (the barrel chamber 37) of the barrel body 36. The cylindrical portion 38 is configured as a female luer having a tapered inner circumferential surface 38a whose outer diameter increases in the distal end direction.

Figure 4:
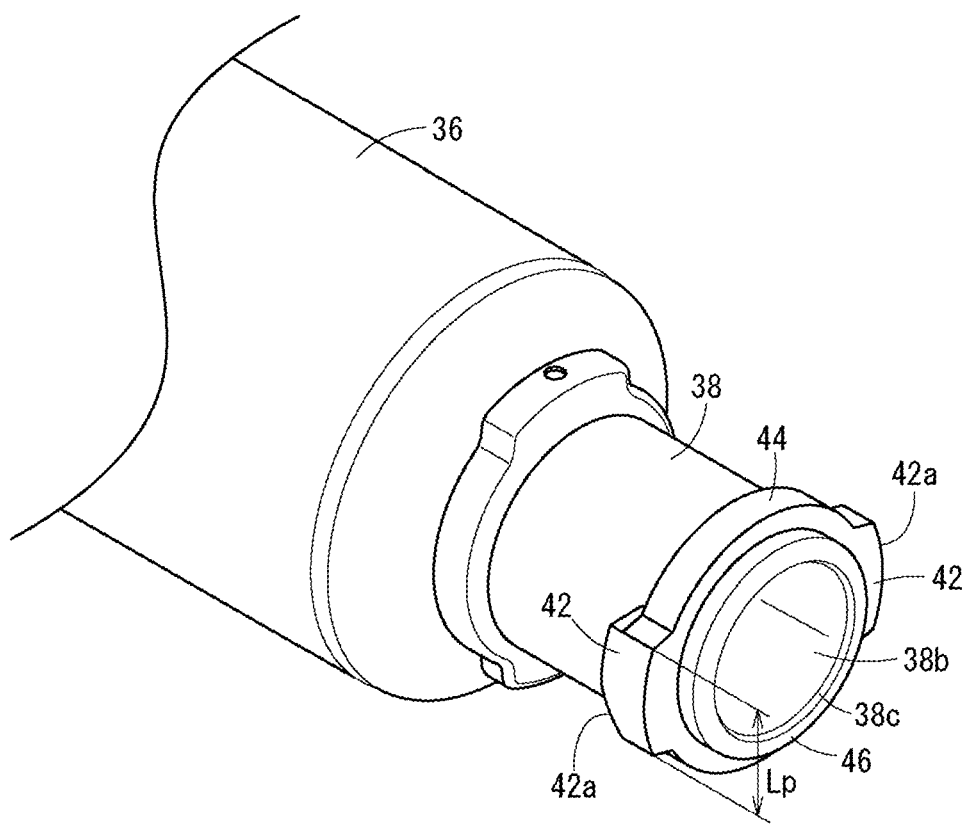
FIG. 4 is a perspective view of a distal end portion of the female syringe barrel.

As illustrated in FIG. 4, two protrusions 42 protruding to outer sides (radially outer sides), opposite to each other with respect to an axis (center line) of the cylindrical portion 38, are provided on an outer circumferential portion at the distal end of the cylindrical portion 38. In accordance with an aspect, the two protrusions 42 have the same shape and size. The two protrusions 42 can be engaged with the screw 28 (see FIG. 2) provided on the lock adapter 26 of the male syringe barrel 16. Each of the protrusions 42 extends in an arc shape in the circumferential direction along an outer circumferential surface of the cylindrical portion 38.

Figure 5:
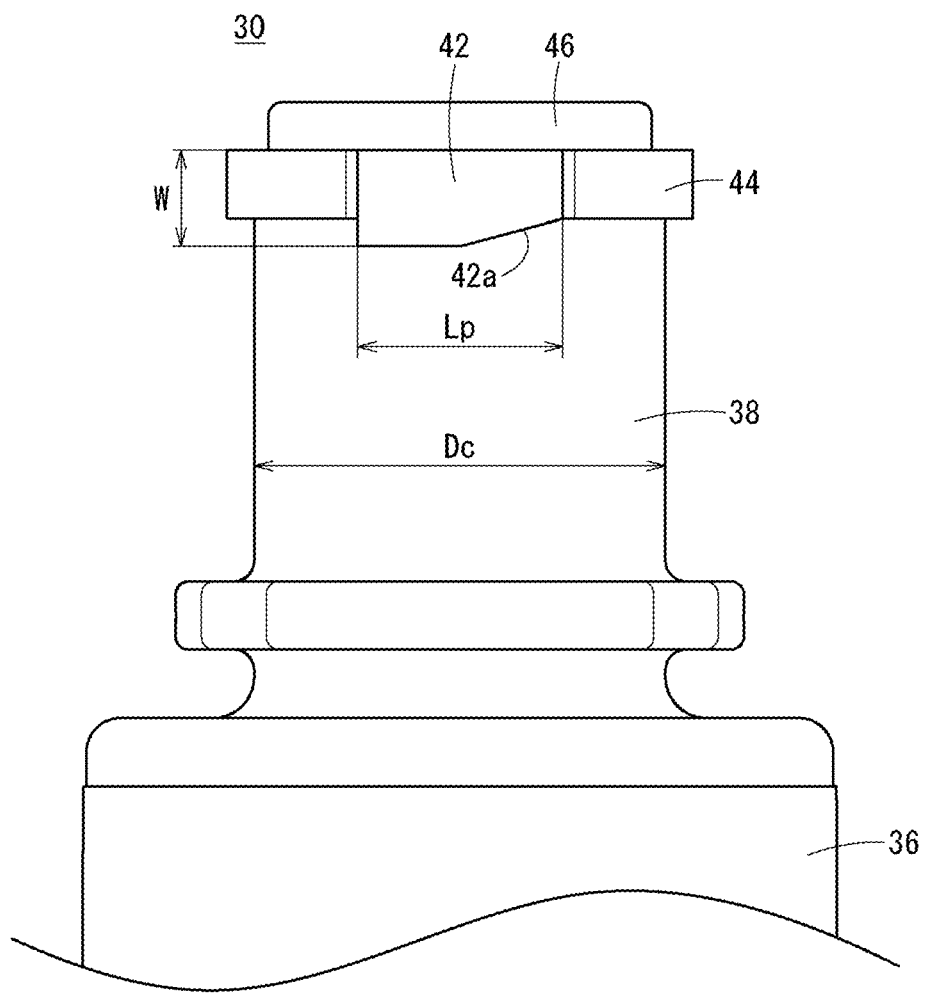
FIG. 5 is a side view of the distal end portion of the female syringe barrel.

In FIG. 5, a length Lp of the protrusion 42 along the radial direction of the cylindrical portion 38 can be, for example, 35% to 65% of an outer diameter Dc of the cylindrical portion 38. Specifically, the length Lp of the protrusion 42 can be, for example, 2.0 mm to 4.5 mm. Note that the length Lp of the protrusion 42 is an external dimension of a protruding end portion of the protrusion 42 in a direction perpendicular to an axis of the cylindrical portion 38 and perpendicular to a direction in which the protrusion 42 protrudes from the cylindrical portion 38 (see also FIG. 4). A width W of the protrusion 42 along the axial direction of the cylindrical portion 38 can be, for example, 1.0 mm to 1.5 mm.

An inclined surface 42a opposing a trailing flank of the screw 28 (see FIG. 2) of the above-described lock adapter 26 is provided at a proximal end portion of the protrusion 42 (an end portion of the protrusion 42 close to the barrel body 36). That is, the inclined surface 42a is inclined with respect to the circumferential direction of the cylindrical portion 38 to be substantially parallel to a spiral extending direction of the screw 28 when the protrusion 42 is engaged with the screw 28.

As illustrated in FIGS. 4 and 5, a ring-shaped protruding portion 44 that protrudes outward from the distal end portion of the cylindrical portion 38 is integrally provided in the female syringe barrel 30 according to the present embodiment. The ring-shaped protruding portion 44 extends in the circumferential direction along the outer circumferential surface of the cylindrical portion 38 with the axis of the cylindrical portion 38 as the center. The ring-shaped protruding portion 44 is continuous with the two protrusions 42. Specifically, the two protrusions 42 are integrally provided on an outer circumferential portion of the ring-shaped protruding portion 44. The two protrusions 42 protrude outward from the outer circumferential portion of the ring-shaped protruding portion 44. The proximal end portion of each of the protrusions 42 protrudes in the proximal end direction (toward the barrel body 36) from a proximal end surface of the ring-shaped protruding portion 44 (an end surface of the ring-shaped protruding portion 44 close to the barrel body 36).

In the female syringe barrel 30 according to the present embodiment, a distal end protruding portion 46 that protrudes in the distal end direction from a distal end portion of the cylindrical portion 38. The distal end protruding portion 46 can be integrally provided (i.e., molded) with the female syringe barrel 30. The distal end protruding portion 46 extends in a ring shape in the circumferential direction concentrically with the cylindrical portion 38. In the present embodiment, an outer diameter of the distal end protruding portion 46 is smaller than the outer diameter Dc of the cylindrical portion 38. Note that the outer diameter of the distal end protruding portion 46 may be the same as the outer diameter Dc of the cylindrical portion 38, or may be larger than the outer diameter Dc of the cylindrical portion 38.

In FIG. 1, the gasket 32 is inserted into the barrel body 36 via the proximal end opening 36a that is open at the proximal end of the barrel body 36. The proximal end side of the barrel body 36 is sealed by the gasket 32 in a liquid-tight manner. The gasket 32 can be made of an elastic material such as a rubber material. The gasket 32 has an outer circumferential portion being in liquid-tight contact with an inner circumferential surface of the barrel body 36 and is arranged to be slidable inside the barrel body 36.

The gasket 32 is connected to a distal end portion of the pusher 34. When a user presses the pusher 34 in the axial direction (distal end direction or proximal end direction), the gasket 32 slides in the axial direction inside the barrel body 36. Note that the pusher 34 may be connected to the gasket 32 at the time of using the female syringe 14.

In an initial state of the female syringe 14, a cap (not illustrated) is mounted on the cylindrical portion 38, and a distal end opening 38c (see FIG. 3) is sealed by this cap. The cap is detached from the cylindrical portion 38 at the time of using the female syringe 14 (at the time of using the syringe kit 10).

The medical liquid ML is a liquid in which the medicine M in the male syringe 12 can be dissolved, diluted, or mixed. Such a medical liquid ML may be a medicine solvent such as a saline solution, a medicine diluent, a medicine mixture, or a medicinal solution containing a medicine (for example, vitamins and minerals). Note that the medical liquid ML is not necessarily poured in the female syringe 14 in advance as in the present embodiment, but may be sucked from, for example, a vial or the like, into the empty female syringe 14 by the required amount as needed.

In the present embodiment, the male syringe barrel 16 and the female syringe barrel 30 are both made of a cyclic polyolefin having high rigidity and high toughness. Note that the male syringe barrel 16 and the female syringe barrel 30 may be made of polyesters such as polypropylene, polyethylene, polystyrene, polyamide, polycarbonate, polyvinyl chloride, poly (4-methylpentene-1), an acrylic resin, an acrylonitrile-butadiene-styrene copolymer, and polyethylene terephthalate.

Next, a method for using the syringe kit 10 configured as described above will be described.

First, the caps (not illustrated) are detached (opened) from the nozzle 24 of the male syringe barrel 16 and the cylindrical portion 38 of the female syringe barrel 30, respectively, in the male syringe 12 and the female syringe 14 illustrated in FIG. 1.

Figure 6:
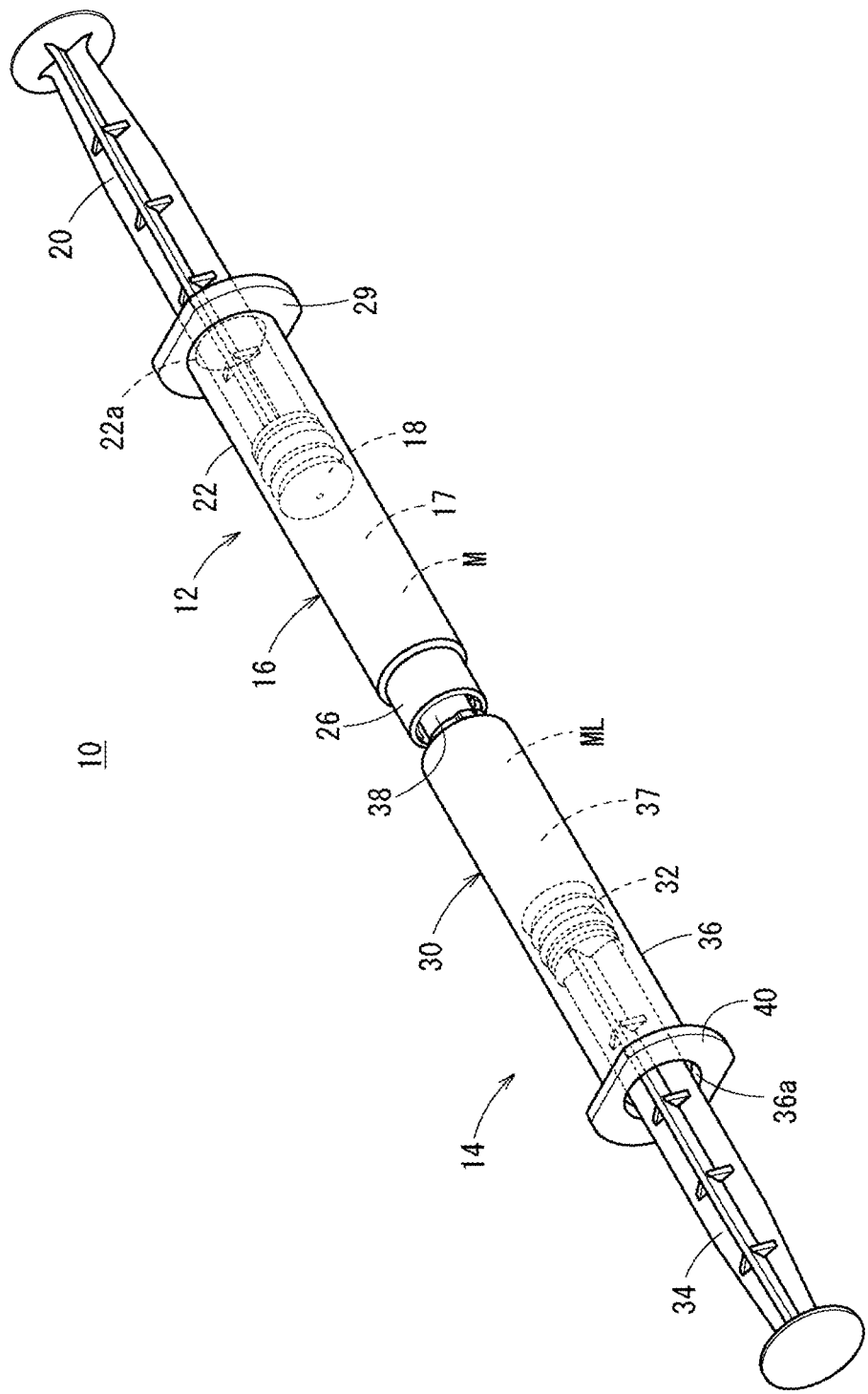
FIG. 6 is a perspective view illustrating a state where a male syringe and a female syringe are connected.

Next, the male syringe barrel 16 and the female syringe barrel 30 are connected to each other as illustrated in FIG. 6. Specifically, the screw 28 (see FIG. 2) of the lock adapter 26 and the protrusion 42 (see FIG. 3) provided on the cylindrical portion 38 of the female syringe barrel 30 are screwed (i.e., engaged). With this screwing, the nozzle 24 (male luer) of the male syringe barrel 16 is inserted into the cylindrical portion 38 (female luer) of the female syringe barrel 30. As a result, the tapered outer circumferential surface 24a (see FIG. 2) of the nozzle 24 is liquid-tightly fitted or tightly connected (i.e., taper-fitted or taper-connected) to the tapered inner circumferential surface 38a (see FIG. 3) of the cylindrical portion 38.

Next, the medical liquid ML and the medicine M are mixed by performing a pumping operation using the pusher 20 of the male syringe 12 and the pusher 34 of the female syringe 14. Specifically, the pusher 34 of the female syringe 14 is pressed in the distal end direction of the female syringe 14 to inject the medical liquid ML from the female syringe barrel 30 into the male syringe barrel 16, thereby mixing the medical liquid ML and the medicine M in the male syringe barrel 16. Next, the pusher 20 of the male syringe 12 is pressed in the distal end direction of the male syringe 12 to inject a mixed liquid (mixture of the medical liquid ML and the medicine M) from the inside of the male syringe barrel 16 into the inside of the female syringe barrel 30. Then, the mixed liquid is repeatedly moved between the male syringe barrel 16 and the female syringe barrel 30 several times to promote dissolution, dilution, or mixing of the medicine M, whereby a desired medicinal solution can be adjusted.

Figure 7:
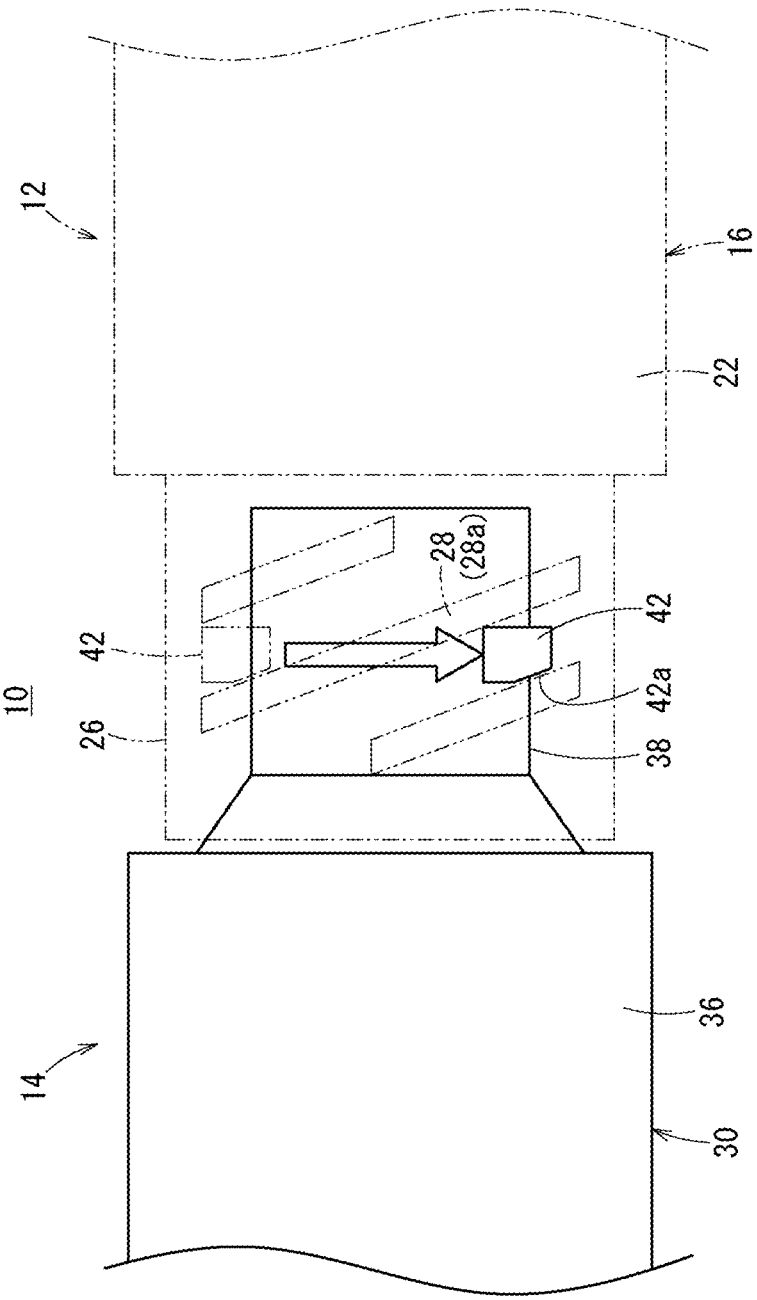
FIG. 7 is a schematic view illustrating a state where a protrusion of the female syringe advances over a screw of the male syringe.

In this case, the cylindrical portion 38 of the female syringe barrel 30 is provided with the two protrusions 42 that can be engaged to the screw 28 of the lock adapter 26 of the male syringe barrel 16 according to the present embodiment. Further, the length Lp of the protrusion 42 along the direction perpendicular to the axis of the cylindrical portion 38 and perpendicular to the direction in which the protrusion 42 protrudes from the cylindrical portion 38 can be, for example, 2.0 mm to 4.5 mm, and the width W of the protrusion 42 along the axial direction of the cylindrical portion 38 can be, for example, 1.0 mm to 2.1 mm. In addition, the inclined surface 42a opposing the trailing flank of the screw 28 of the lock adapter 26 is provided at the end portion of the protrusion 42 close to the barrel body 36. For this reason, when the excessive torque is applied at the time of screwing the protrusion 42 and the screw 28 of the lock adapter 26, the protrusion 42 advances over the screw thread 28a of the lock adapter 26 (the protrusion 42 idles) as schematically illustrated in FIG. 7. Note that the protrusion 42 indicated by the virtual line in FIG. 7 is the protrusion 42 before advancing over the screw thread 28a.

That is, when the screwing between the protrusion 42 and the screw 28 progresses to a certain extent, the fitting between the tapered outer circumferential surface 24a of the nozzle 24 and the tapered inner circumferential surface 38a of the cylindrical portion 38 is completed. Then, when the screw 28 is further engaged from this state, mainly the screw 28 (the lock adapter 26) is elastically deformed outward, so that the protrusion 42 advances over the screw thread 28a. Note that the expression that "the protrusion 42 advances over the screw thread 28a" does not mean that the protrusion 42 moves along the spiral shape of the screw 28, but means that the protrusion 42 moves from one side of the screw thread 28a to the other side across the top of the screw thread 28a.

Since the protrusion 42 advances over the screw thread 28a in this manner, no further relative displacement in the axial direction between the protrusion 42 and the screw 28 accompanying the screwing occurs, so that the nozzle 24 and the cylindrical portion 38 are not excessively connected (i.e., engaged). As a result, excessive tightening can be prevented, damage and deformation of the cylindrical portion 38 of the female syringe barrel 30 can be prevented, and deterioration in liquid tightness between the nozzle 24 and the cylindrical portion 38 can be prevented.

Meanwhile, a male reference connector is specified in ISO594-2 (i.e., International Organization for Standardization 594-2) as a connector for testing a locking connector using screw connection. In the present embodiment, the protrusion 42 advances over the screw thread 28a of the lock adapter 26 at the time of screwing the screw 28 and the protrusion 42 by a torque smaller than a torque at which the female syringe 14 is damaged when a convex reference conical fitting for the stress crack test specified in ISO 594-2 is engaged with the female syringe 14. For this reason, it is possible to more reliably prevent the cylindrical portion 38 of the female syringe 14 from being damaged. Note that the convex reference conical fitting is made of a material having corrosion resistance (for example, stainless steel).

In the present embodiment, the ring-shaped protruding portion 44 (see FIG. 4) protrudes outward from the distal end portion of the cylindrical portion 38, and the protrusion 42 is formed on the outer circumferential portion of the ring-shaped protruding portion 44. As a result, the protrusion 42 and the cylindrical portion 38 can be reinforced. Therefore, when the protrusion 42 advances over the screw thread 28a of the lock adapter 26, the protrusion 42 and the cylindrical portion 38 are less likely to be deformed, and the liquid tightness between the nozzle 24 and the cylindrical portion 38 can be favorably kept.

In the present embodiment, the distal end protruding portion 46 (see FIG. 4) protrudes from the distal end portion of the cylindrical portion 38 toward the distal end, and the distal end protruding portion 46 is located to be closer to the distal end than the protrusion 42. As a result, the protrusion 42 and the cylindrical portion 38 can be reinforced. Therefore, when the protrusion 42 advances over the screw thread 28a of the lock adapter 26, the protrusion 42 and the cylindrical portion 38 are less likely to be deformed, and the liquid tightness between the nozzle 24 and the cylindrical portion 38 can be favorably kept.

Since the female syringe barrel 30 is made of the cyclic polyolefin having a relatively high rigidity and toughness in the present embodiment, when the protrusion 42 advances over the screw thread 28a of the lock adapter 26, the protrusion 42 and the cylindrical portion 38 are less likely to be deformed, and the liquid tightness between the nozzle 24 and the cylindrical portion 38 can be favorably kept. In addition, since the male syringe barrel 16 is also made of the cyclic polyolefin having a relatively high rigidity and toughness in the present embodiment, when the protrusion 42 advances over the screw thread 28a of the lock adapter 26, the nozzle 24 is less likely to be deformed, and the liquid tightness between the nozzle 24 and the cylindrical portion 38 is kept more favorable.

In the present embodiment, both the outer diameter D1 of the barrel body 22 of the male syringe barrel 16 and the outer diameter D2 of the barrel body 36 of the female syringe barrel 30 are 6.7 mm or larger. In addition, both the axial length L1 of the barrel body 22 of the male syringe barrel 16 and the axial length L2 of the barrel body 36 of the female syringe barrel 30 are 35 mm or longer. In general, in the case of a barrel for a syringe, provided with a barrel body having the above external dimensions, screwing is performed by gripping the barrel body, and thus, the screwing can be reliably performed, but it is easy to apply a strong torque so that it is easy to cause breakage or deformation. According to the present disclosure, however, the protrusion 42 advances over the screw thread 28a even if the barrel bodies 22 and 36 have the above-described external dimensions, and thus, it is possible to prevent the damage and deformation of the cylindrical portion 38 as described above, and the deterioration in liquid tightness between the nozzle 24 and the cylindrical portion 38 can be effectively prevented. Therefore, the present disclosure is particularly useful when the barrel bodies 22 and 36 have the above-described external dimensions.

In the present embodiment, the two protrusions 42 advance over the screw thread 28a of the lock adapter 26 by the predetermined torque at the time of screwing the screw 28 and the two protrusions 42, and the protrusions 42 (and the screw 28) generate the click feeling along with the advancement. For this reason, the user who has performed the screwing operation can rather easily know that the screwing between the protrusions 42 and the screw 28 has been completed based on the generated click feeling, and it is possible to quickly shift to the next step (the above-described mixing operation). Note that the protrusions 42 (and the screw 28) may generate a click sound together with the click feeling.

Figure 8:
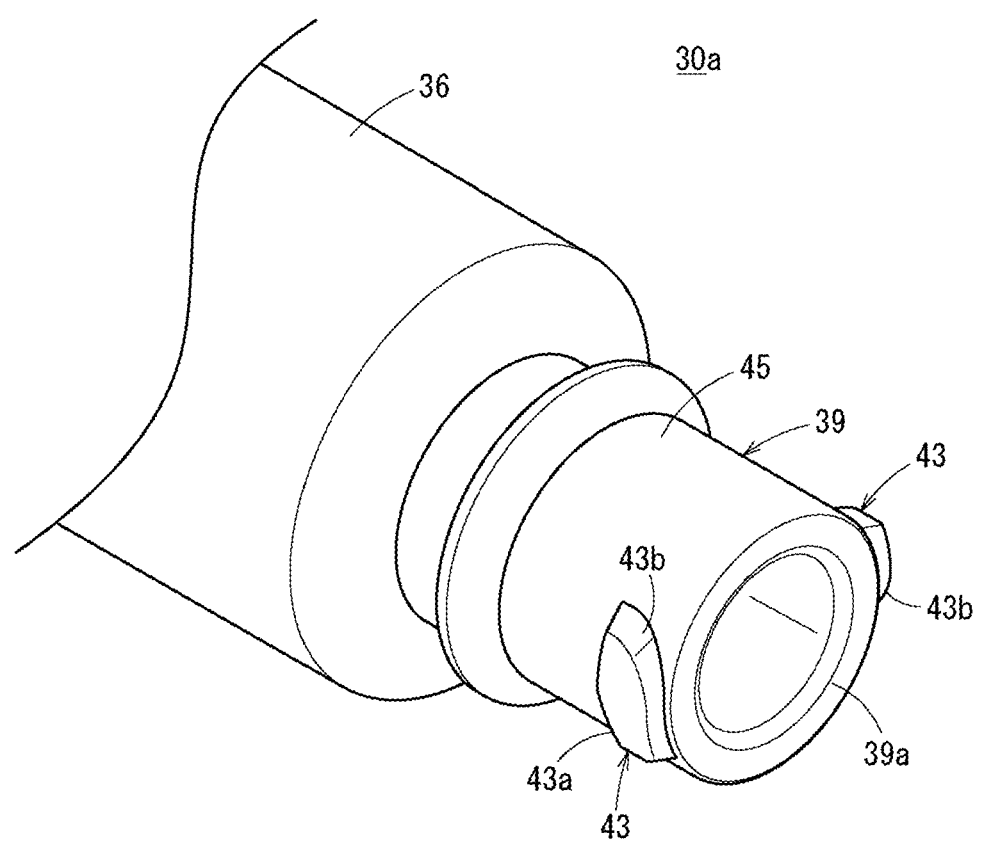
FIG. 8 is a perspective view of a distal end portion of a female syringe barrel according to a first modification.
Figure 9:
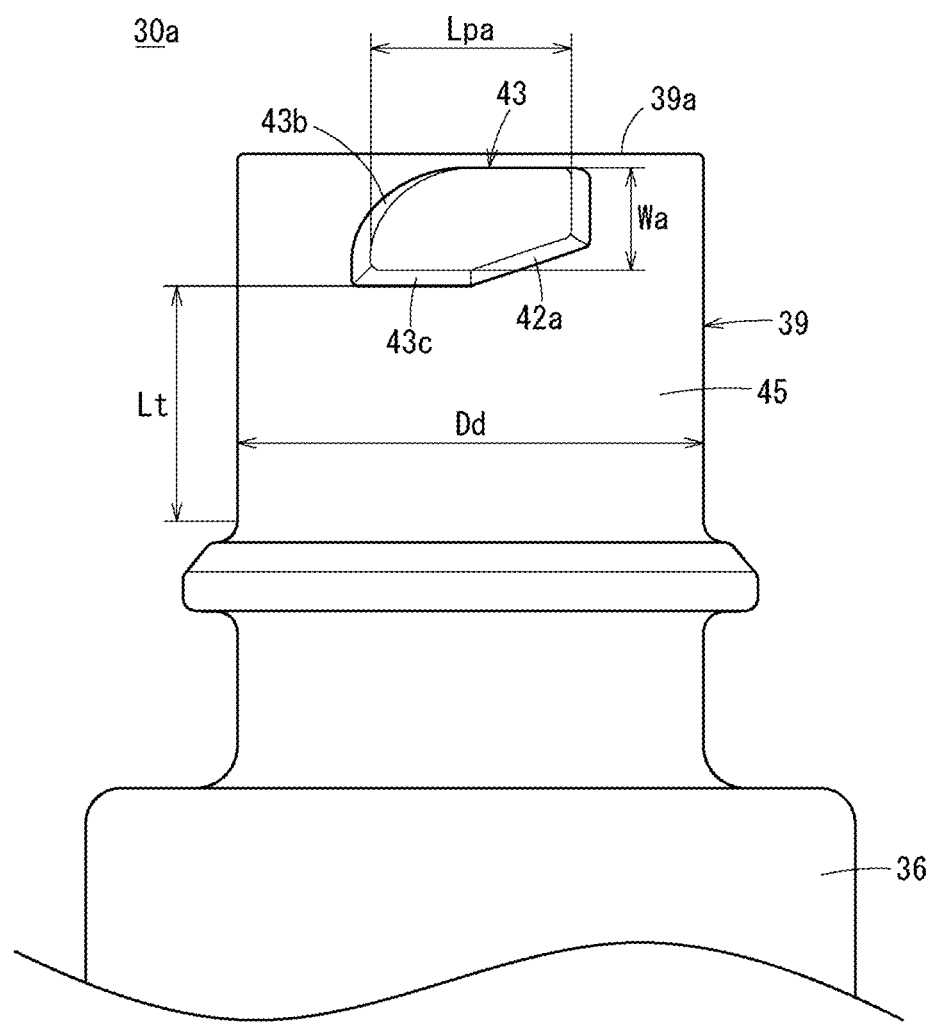
FIG. 9 is a side view of the distal end portion of the female syringe barrel according to the first modification.

In the above-described syringe kit 10, a female syringe barrel 30a according to a first modification illustrated in FIGS. 8 and 9 may be adopted, instead of the female syringe barrel 30. The female syringe barrel 30a is different from the female syringe barrel 30 illustrated in FIG. 1 in terms that a cylindrical portion 39 is provided instead of the cylindrical portion 38. As illustrated in FIG. 8, the cylindrical portion 39 has two protrusions 43, which can be engaged with the screw 28 (see FIG. 10) provided on the lock adapter 26 of the male syringe 12, on opposite sides on an outer circumferential portion of the cylindrical portion 39.

In FIG. 9, a length Lpa of each of the protrusions 43 (the top of each of the protrusions 43) along the radial direction of the cylindrical portion 39 can be, for example, 2.7 mm to 3.5 mm. A width Wa of each of the protrusions 43 (the top of each of the protrusions 43) along the axial direction of the cylindrical portion 39 can be, for example, 1.5 mm to 2.1 mm. Note that the length Lpa of each of the protrusions 43 may be, for example, 2.0 mm to 4.5 mm similarly to the length Lp of each of the protrusions 42, and the width Wa of each of the protrusions 43 may be, for example, 1.0 mm to 2.1 mm similarly to the width W of each of the protrusions 42.

As illustrated in FIG. 8, each of the two protrusions 43 of the female syringe barrel 30a is provided with an inclined surface 43a opposing the trailing flank of the screw 28 of the lock adapter 26 when the two protrusions 43 are engaged with the screw 28 of the lock adapter 26. The inclined surface 43a is configured in the same manner as the inclined surface 42a (see FIG. 5) provided on each of the protrusions 42 of the female syringe barrel 30 described above. Each of the protrusions 43 has a chamfered corner 43b chamfered on a side surface opposing the inclined surface 42a. The chamfered corner 43b is an arcuate curved surface.

Figure 10:
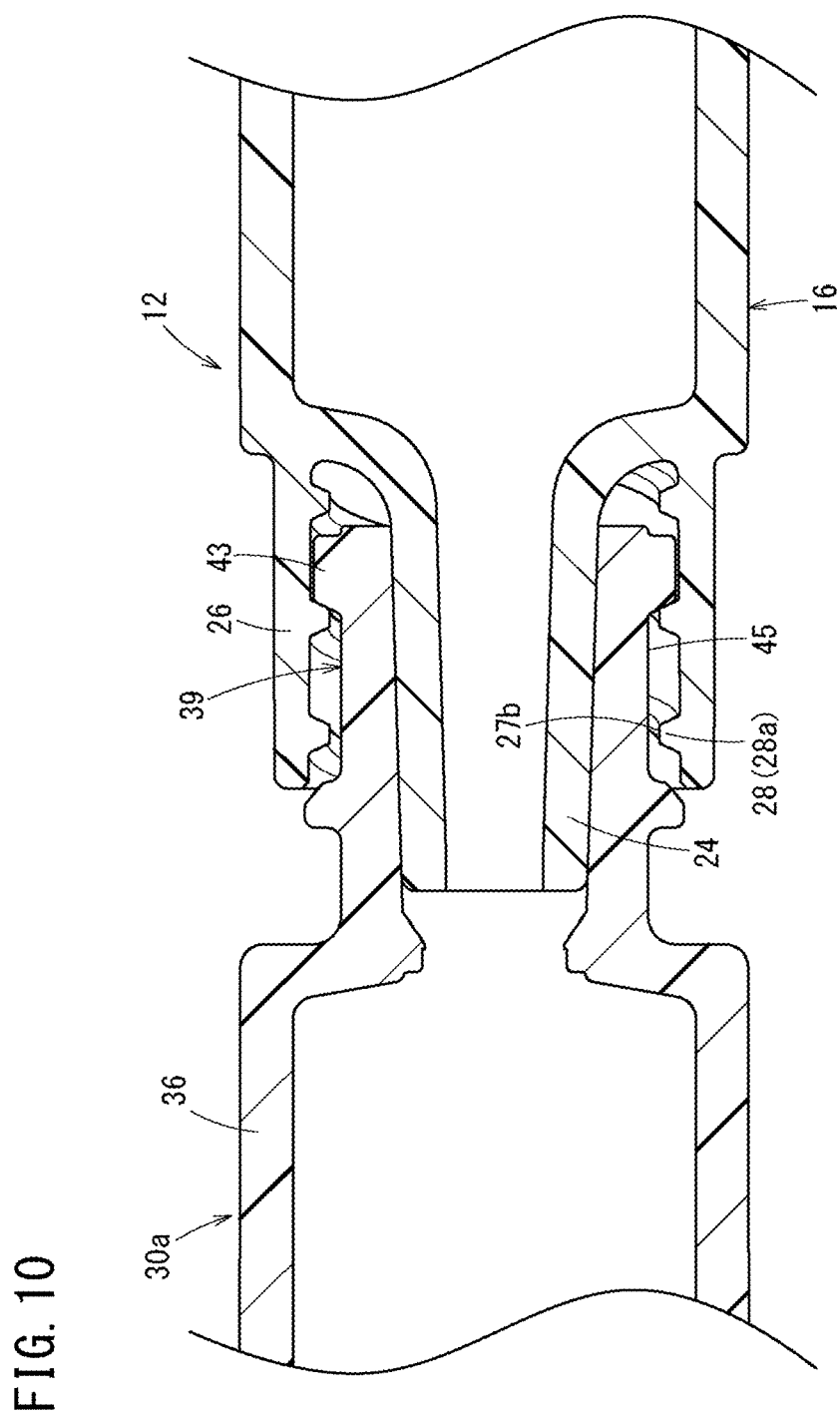
FIG. 10 is a cross-sectional view of a state where the female syringe barrel and a male syringe barrel according to a first modification are connected.

The cylindrical portion 39 includes an abutment portion 45 having an outer diameter Dd of 6.4 mm to 6.8 mm at a position closer to a proximal end than the two protrusions 43 on the outer circumferential portion of the cylindrical portion 39. As illustrated in FIG. 10, when the two protrusions 43 of the cylindrical portion 39 are engaged with the screw 28 of the lock adapter 26 of the male syringe 12, the abutment portion 45 abuts on an inner circumferential surface 27b of the screw 28 of the lock adapter 26 so as to suppress an inclination of an axis of the cylindrical portion 39 with respect to an axis of the lock adapter 26.

As illustrated in FIG. 9, the outer diameter Dd of the abutment portion 45 is constant along the axial direction of the cylindrical portion 39. The abutment portion 45 in the illustrated example is an annular surface (cylindrical surface) that extends over the entire circumference about the axis of the cylindrical portion 39. An external shape of the abutment portion 45 in a cross section perpendicular to the axis of the cylindrical portion 39 is not limited to a circle, but may be, for example, a non-circular shape such as a polygon. The abutment portion 45 may be present partially on the outer circumferential portion in the circumferential direction instead of the entire outer circumferential portion of the cylindrical portion 39.

The abutment portion 45 is provided continuously from proximal ends 43c of the two protrusions 43 to a position separated, for example, by at least 4 mm from a distal end 39a of the cylindrical portion 39 to the barrel body 36. A length Lt of the abutment portion 45 along the axial direction of the cylindrical portion 39 is preferably larger than the width Wa of the protrusion 43.

Even in the case of adopting this female syringe barrel 30a, the protrusion 43 advances over the screw thread 28a of the lock adapter 26 when an excessive torque is applied at the time of screwing the protrusion 43 and the screw 28 of the lock adapter 26 as illustrated in FIG. 10. For this reason, excessive tightening can be prevented, damage and deformation of the cylindrical portion 39 of the female syringe barrel 30a can be prevented, and deterioration in liquid tightness between the nozzle 24 and the cylindrical portion 39 can be prevented.

In addition, the female syringe barrel 30a includes the abutment portion 45 having the outer diameter Dd of 6.4 mm to 6.8 mm at the position closer to the proximal end than the two protrusions 43 on the outer circumferential portion of the cylindrical portion 39. Therefore, the abutment portion 45 abuts on the inner circumferential surface 27b of the screw 28 of the lock adapter 26 when the two protrusions 43 of the cylindrical portion 39 are engaged with the screws 28 of the lock adapter 26 of the male syringe 12 as illustrated in FIG. 10, so that the inclination of the axis of the cylindrical portion 39 with respect to the axis of the lock adapter 26 can be suppressed. For this reason, the cylindrical portion 39 can be prevented from breaking by being engaged with the axis being inclined.

That is, if the cylindrical portion 39 is engaged with the axis of the lock adapter 26 being inclined with respect to the axis of the lock adapter 26, there is a possibility that the cylindrical portion 39 breaks because stress applied to the cylindrical portion 39 becomes uneven in the circumferential direction. However, according to the female syringe barrel 30a, the abutment portion 45 suppresses the inclination of the axis of the cylindrical portion 39 with respect to the axis of the lock adapter 26 as described above, and thus, it is possible to help prevent the breakage of the cylindrical portion 39 due to the uneven stress in the circumferential direction.

In FIG. 9, the length Lpa of the protrusion 43 can be, for example, 2.7 mm to 3.5 mm, the width Wa of the protrusion 43 can be, for example, 1.5 mm to 2.1 mm, and the protrusion 43 has the chamfered corner 43b chamfered on the side surface opposing the inclined surface 43a. With the above chamfered corner 43b, a corner of the protrusion 43 does not interfere with the screw 28 when the protrusion 43 is large.

Figure 11:
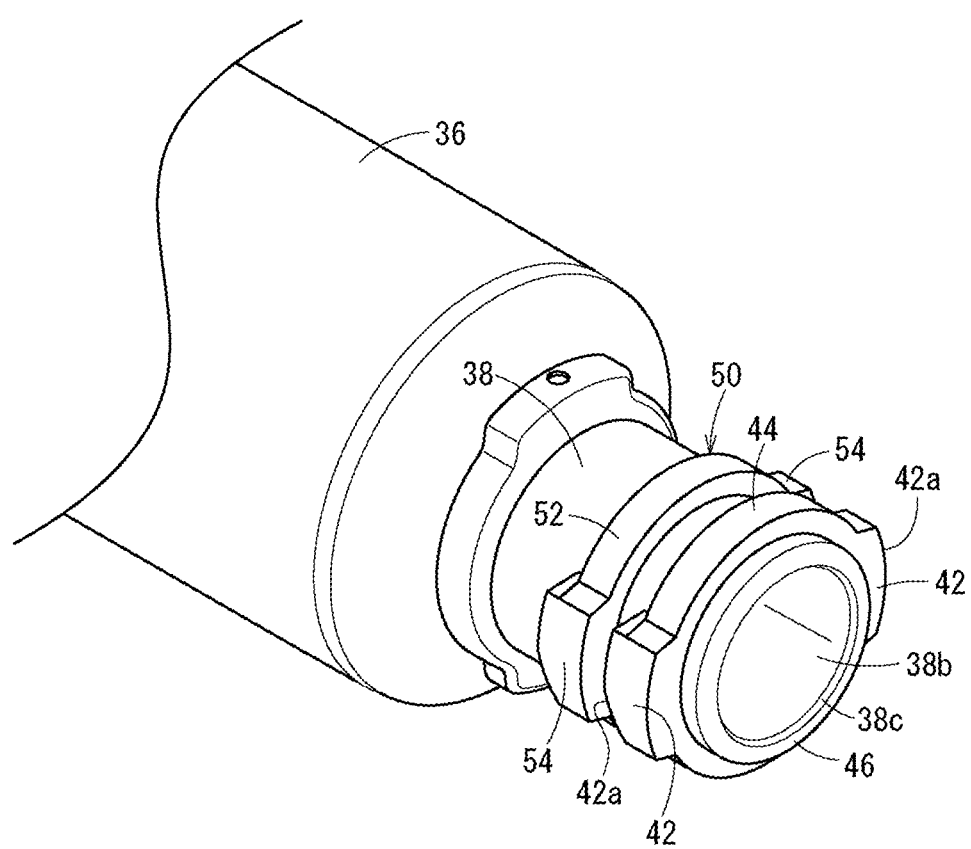
FIG. 11 is a perspective view of a female syringe barrel according to a second modification.

In the above-described syringe kit 10, a female syringe barrel 30A according to a second modification illustrated in FIG. 11 may be adopted instead of the female syringe barrel 30. This female syringe barrel 30A is obtained by adding a proximal-end-side protruding portion 50 to the female syringe barrel 30 illustrated in FIG. 1 and the like. The proximal-end-side protruding portion 50 protrudes from the outer circumferential portion of the cylindrical portion 38 and is provided at a position closer to the proximal end than the protrusion 42 with an interval in the axial direction of the cylindrical portion 38.

Specifically, the proximal-end-side protruding portion 50 includes a proximal-end-side ring-shaped protruding portion 52 that protrudes outward from the outer circumferential portion of the cylindrical portion 38 and two proximal-end-side protrusions 54 that protrude to outer sides, opposite to each other, with reference to the axis of the cylindrical portion 38. The proximal-end-side ring-shaped protruding portion 52 has the same configuration as the ring-shaped protruding portion 44. The two proximal-end-side protrusions 54 are provided on an outer circumferential portion of the proximal-end-side ring-shaped protruding portion 52, and have the same configuration as the two protrusions 42. In the cylindrical portion 38, the two proximal-end-side protrusions 54 are provided at the same circumferential positions as the two protrusions 42.

Figure 12A:
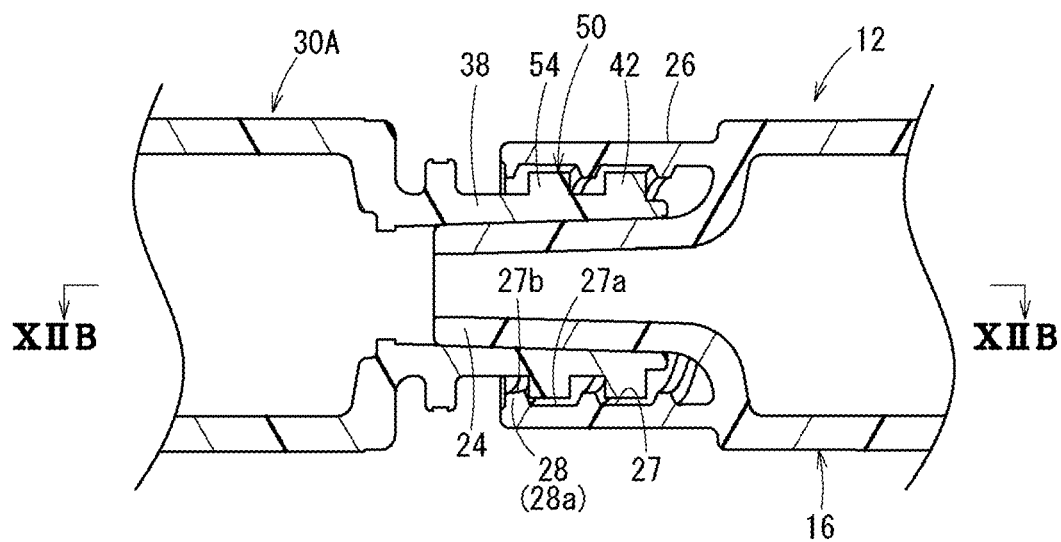
FIG. 12A is a cross-sectional view illustrating a state where the female syringe barrel and a male syringe barrel according to a second modification are connected.
Figure 12B:
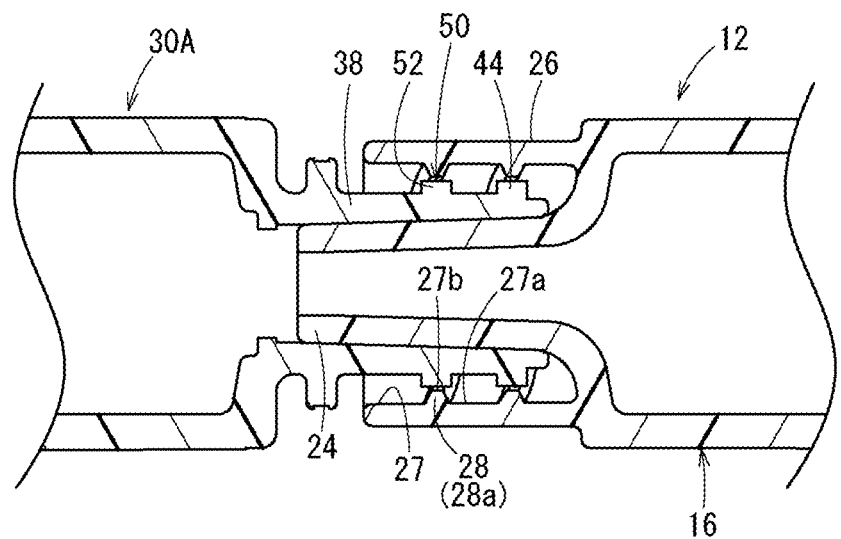
FIG. 12B is a cross-sectional view taken along the section line XIIB-XIIB in FIG. 12A.

In this manner, the proximal-end-side protruding portion 50 protruding from the outer circumferential portion of the cylindrical portion 38 is provided at a position closer to the proximal end than the two protrusions 42 in the female syringe barrel 30A. Therefore, the proximal-end-side protruding portion 50 abuts on an inner circumferential surface 27 of the lock adapter 26 when the two protrusions 42 of the cylindrical portion 38 are engaged with the screw 28 of the lock adapter 26 of the male syringe 12 as illustrated in FIGS. 12A and 12B, so that the inclination of the axis of the cylindrical portion 38 with respect to the axis of the lock adapter 26 is suppressed. For this reason, the cylindrical portion 38 can be prevented from breaking by being engaged with the axis being inclined.

That is, for example, if the cylindrical portion 38 is engaged with the axis of the lock adapter 26 being inclined with respect to the axis of the lock adapter 26, there is a possibility that the cylindrical portion 38 breaks because stress applied to the cylindrical portion 38 becomes uneven in the circumferential direction. However, according to the female syringe barrel 30A, the proximal-end-side protruding portion 50 suppresses the inclination of the axis of the cylindrical portion 38 with respect to the axis of the lock adapter 26 as described above, and thus, it is possible to help prevent the breakage of the cylindrical portion 38 due to the uneven stress in the circumferential direction.

In this case, the inclination of the axis is prevented as the proximal-end-side protrusion 54 abuts on at least one of an inner circumferential surface 27a between the screw threads 28a of the lock adapter 26 and the inner circumferential surface 27b of the screw thread 28a of the lock adapter 26 during the screwing. That is, during the screwing, the proximal-end-side protrusion 54 opposes the inner circumferential surface 27a between the screw threads 28a of the lock adapter 26 (FIG. 12A), and the proximal-end-side ring-shaped protruding portion 52 opposes the inner circumferential surface 27b of the screw thread 28a of the lock adapter 26 (FIG. 12B). Accordingly, in the female syringe barrel 30A in the illustrated example, the inclination of the axis is prevented as the proximal-end-side protrusion 54 and the proximal-end-side ring-shaped protruding portion 52 function as abutment portions that abut on the inner circumferential surface 27a between the screw threads 28a of the lock adapter 26 and the inner circumferential surface 27b of the screw thread 28a of the lock adapter 26, respectively, during the screwing. In this manner, the inner circumferential surface 27 of the lock adapter 26 includes the inner circumferential surface 27a between the screw threads 28a and the inner circumferential surface 27b of the screw thread 28a.

Note that, during the screwing, the proximal-end-side protrusion 54 may abut on the inner circumferential surface 27a between the screw threads 28a of the lock adapter 26, and the proximal-end-side ring-shaped protruding portion 52 does not necessarily abut on the inner circumferential surface 27b of the screw thread 28a of the lock adapter 26. Alternatively, during the screwing, the proximal-end-side ring-shaped protruding portion 52 may abut on the inner circumferential surface 27b of the screw thread 28a of the lock adapter 26, and the proximal-end-side protrusion 54 does not necessarily abut on the inner circumferential surface 27a between the screw threads 28a of the lock adapter 26. In addition, the proximal-end-side protrusion 54 may be omitted, and the proximal-end-side ring-shaped protruding portion 52 may function as the abutment portion that abuts on the inner circumferential surface 27b of the screw thread 28a of the lock adapter 26 during the screwing. In this case, the outer diameter of the proximal-end-side ring-shaped protruding portion 52 is preferably, for example, 6.4 mm to 6.8 mm.

Even in the case of adopting this female syringe barrel 30A, the protrusion 42 advances over the screw thread 28a of the lock adapter 26 as schematically illustrated in FIG. 13 when an excessive torque is applied at the time of screwing the protrusion 42 and the screw 28 of the lock adapter 26. At this time, the proximal-end-side protrusion 54 also advances over the screw thread 28a similarly to the protrusion 42. For this reason, excessive tightening can be prevented, damage and deformation of the cylindrical portion 38 of the female syringe barrel 30A can be prevented, and deterioration in liquid tightness between the nozzle 24 and the cylindrical portion 38 can be prevented.

Figure 14:
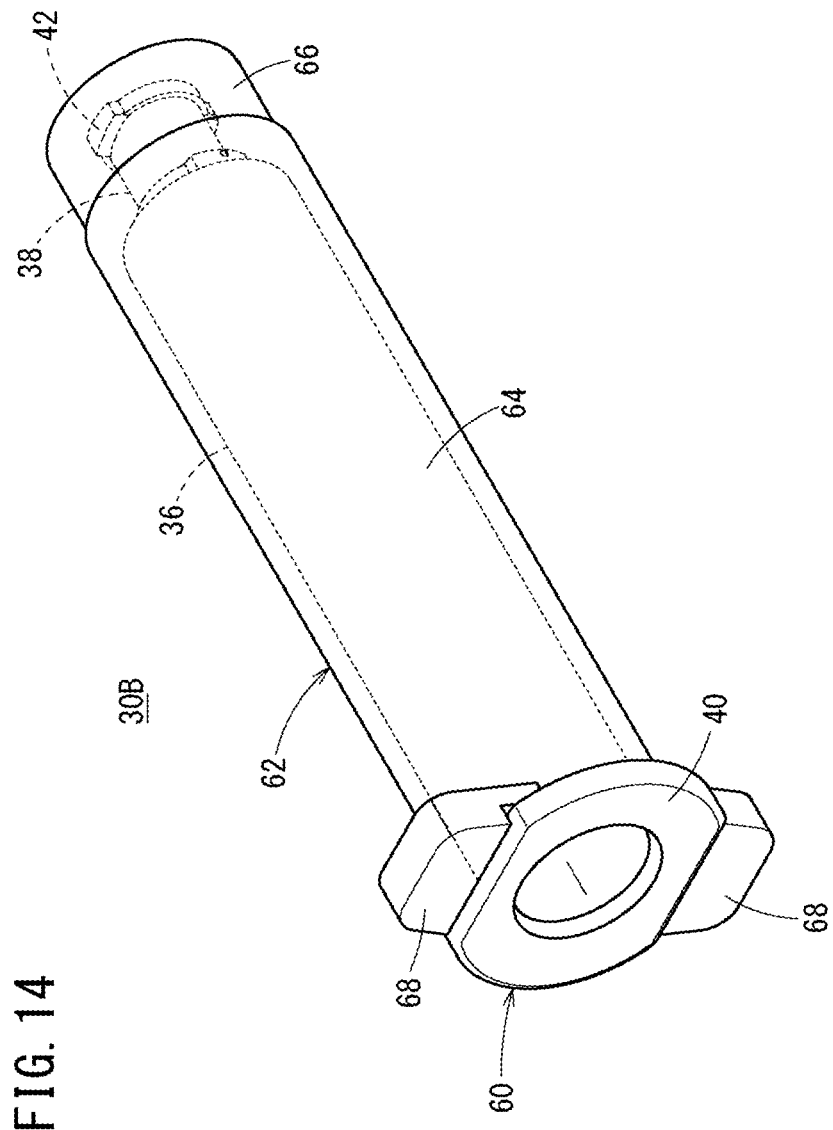
FIG. 14 is a perspective view of a female syringe barrel according to a third modification.

In the above-described syringe kit 10, a female syringe barrel 30B according to a third modification illustrated in FIG. 14 may be adopted instead of the female syringe barrel 30. The female syringe barrel 30B has a female barrel main body 60 and an outer cylinder 62 that surrounds an outer circumferential portion of the cylindrical portion 38 of the female barrel main body 60 and is not rotatable with respect to the cylindrical portion 38. The female barrel main body 60 has the same configuration as the above-described female syringe barrel 30, and thus, its components are denoted by the same reference signs as those of the female syringe barrel 30.

The outer cylinder 62 illustrated in FIG. 14 is configured to be detachable from the female barrel main body 60. Specifically, the outer cylinder 62 has: a body portion 64 that covers the barrel body 36 of the female barrel main body 60; a distal end cylindrical portion 66 extending in a distal end direction from a distal end of the body portion 64; and a pair of engagement portions 68 protruding to outer sides, opposite to each other, from a proximal end of the body portion 64.

In accordance with an embodiment, the outer cylinder 62 is made of a transparent material (for example, the same material as the female barrel main body 60) such that the female barrel main body 60 (and the inside of the female barrel main body 60) arranged inside can be visually recognized. The distal end cylindrical portion 66 is a hollow cylindrical body surrounding the cylindrical portion 38 of the female barrel main body 60, and is arranged concentrically with the cylindrical portion 38. An annular space is formed between the distal end cylindrical portion 66 and the cylindrical portion 38.

Figure 15:
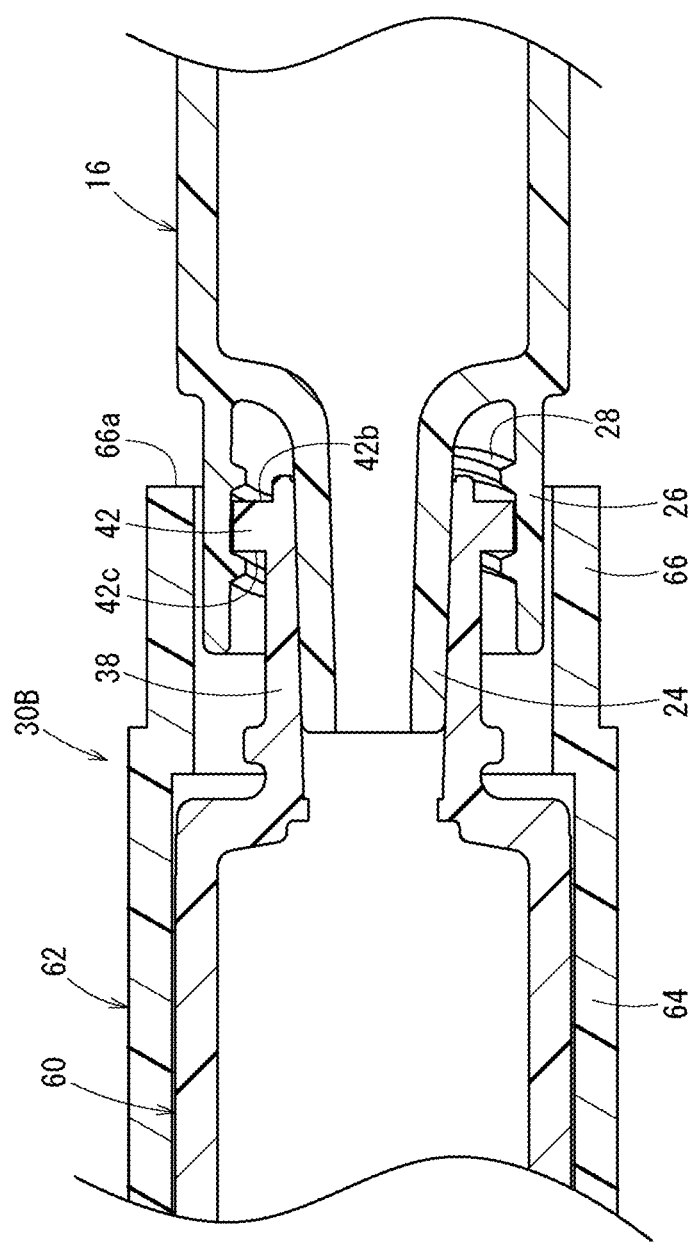
FIG. 15 is a cross-sectional view of a state where the female syringe barrel and a male syringe barrel according to a third modification are connected.

The distal end cylindrical portion 66 is formed so as to cover the protrusion 42 provided on the cylindrical portion 38. Specifically, in a state where the outer cylinder 62 is mounted on the female barrel main body 60 as illustrated in FIG. 15, a distal end surface 66a of the distal end cylindrical portion 66 is located to be closer to the distal end than a distal end surface 42b of the protrusion 42 provided on the cylindrical portion 38. Note that the distal end surface 66a of the distal end cylindrical portion 66 may be located at an axial position between the distal end surface 42b and a proximal end surface 42c of the protrusion 42. An inner diameter of the distal end cylindrical portion 66 can be slightly larger than an outer diameter of the lock adapter 26 of the male syringe barrel 16.

In FIG. 14, the pair of engagement portions 68 is engaged with edges of the flange 40 of the female barrel main body 60 on both sides in the short-axis direction. As a result, the outer cylinder 62 is not rotatable with respect to the female barrel main body 60. A hook that engages with a proximal end surface of the flange 40 may be provided on the engagement portion 68 such that the outer cylinder 62 is not detached from the female barrel main body 60.

In this manner, the outer cylinder 62 that surrounds the outer circumferential portion of the cylindrical portion 38 and is not rotatable with respect to the cylindrical portion 38 is provided in the female syringe barrel 30B. Therefore, as illustrated in FIG. 15, when the two protrusions 42 of the cylindrical portion 38 are engaged with the screw 28 of the lock adapter 26 of the male syringe 12, the lock adapter 26 is inserted between the cylindrical portion 38 and the outer cylinder 62. At this time, an inner circumferential surface of the outer cylinder 62 abuts on the outer circumferential surface of the lock adapter 26, thereby suppressing the inclination of the axis of the cylindrical portion 38 with respect to the axis of the lock adapter 26. For this reason, the cylindrical portion 38 can be prevented from breaking by being engaged with the axis being inclined.

Note that the outer cylinder 62 is not limited to the shape that surrounds most of the female barrel main body 60 as described above, and may be formed integrally with the female barrel main body 60 only around the cylindrical portion 38.

Although the case where the male syringe 12 is filled with the medicine M, and the female syringe 14 is filled with the medical liquid ML has been exemplified in the above-described embodiment, the fillings may be reversed between the male syringe 12 and the female syringe 14. That is, the male syringe 12 may be filled with the medical liquid ML, and the female syringe 14 may be filled with the medicine M.

The present disclosure is not limited to the above-described embodiment, and various modifications can be made within a scope not departing from a gist of the present disclosure.

The detailed description above describes embodiments of a female syringe barrel, a syringe kit, and a syringe connection method. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A syringe kit comprising:
    a male syringe having a male syringe barrel that includes a nozzle configured as a male luer, a lock adapter which surrounds an outer circumferential surface of the nozzle and has a screw on an inner circumferential surface of the lock adapter, and a male barrel body connected to the nozzle and the lock adapter;
    a female syringe having a female syringe barrel that includes a cylindrical portion configured as a female luer to which the nozzle is connectable, two protrusions which protrude from an outer circumferential surface of the cylindrical portion and are engageable with the screw of the lock adapter, and a female barrel body connected to the cylindrical portion;
    each of the two protrusions has an inclined surface;
    when the screw and the two protrusions are engaged, the two protrusions which each have the inclined surface are configured to advance over a screw thread of the lock adapter by a torque smaller than a torque at which the female syringe breaks when the female syringe is engaged with a convex reference conical fitting for a stress crack test specified in ISO 594-2; and
    wherein the two protrusions each have a chamfered corner chamfered on a side opposing the inclined surface.

2. The syringe kit according to claim 1, wherein the male syringe barrel and the female syringe barrel are both made of a cyclic polyolefin.

3. The syringe kit according to claim 1, further comprising:
    an outer diameter of the male barrel body and an outer diameter of the female barrel body are both 6.7 mm or larger; and
    an axial length of the male barrel body and an axial length of the female barrel body are both 35 mm or longer.

4. The syringe kit according to claim 1, further comprising:
    an inner diameter of the screw of the lock adapter is 6.8 mm to 7.2 mm; and
    the cylindrical portion includes an abutment portion provided at a position closer to a proximal end than the two protrusions on an outer circumferential portion of the cylindrical portion.

5. The syringe kit according to claim 4, wherein
    the abutment portion has an outer diameter of 6.4 mm to 6.8 mm; and
    the abutment portion is configured to abut on an inner circumferential surface of the screw of the lock adapter so as to suppress an inclination of an axis of the cylindrical portion with respect to an axis of the lock adapter when the two protrusions of the cylindrical portion are engaged with the screw of the lock adapter of the male syringe.

6. The syringe kit according to claim 5, wherein the abutment portion is continuous from a proximal end of each of the two protrusions to a position separated by at least 4 mm toward the female barrel body from a distal end of the cylindrical portion.

7. The syringe kit according to claim 1, wherein the inclined surface of each of the two protrusions is configured to oppose a trailing flank of the screw of the lock adapter when the two protrusions are engaged with the screw of the lock adapter.

8. The syringe kit according to claim 1, wherein the chamfered corner is an arcuate curved surface.

9. The syringe kit according to claim 1, further comprising:
    a length of each of the two protrusions along a direction, perpendicular to an axis of the cylindrical portion and perpendicular to a direction in which each of the two protrusions protrudes from the cylindrical portion, is 2.0 mm to 4.5 mm; and
    a width of each of the two protrusions along an axial direction of the cylindrical portion is 1.0 mm to 2.1 mm.

10. The syringe kit according to claim 1, further comprising:
    a distal end protruding portion protruding from a distal end portion of the cylindrical portion of the female syringe toward a distal end, and wherein the distal end protruding portion is closer to the distal end than the two protrusions.

11. The syringe kit according to claim 1, wherein
    the cylindrical portion of the female syringe has a proximal-end-side protruding portion that protrudes from an outer circumferential portion of the cylindrical portion and is provided at a position closer to a proximal end than one of the two protrusions; and
    the proximal-end-side protruding portion is configured to abut on the inner circumferential surface of the lock adapter and configured to suppress an inclination of an axis of the cylindrical portion with respect to an axis of the lock adapter when the two protrusions of the cylindrical portion are engaged with the screw of the lock adapter of the male syringe.

12. The syringe kit according to claim 1, wherein
    the cylindrical portion includes an abutment portion having an outer diameter of 6.4 mm to 6.8 mm on an outer circumferential portion of the cylindrical portion;
    the abutment portion is closer to a proximal end than the two protrusions; and
    the abutment portion is configured to abut on an inner circumferential surface of the screw of the lock adapter and configured to suppress an inclination of an axis of the cylindrical portion with respect to an axis of the lock adapter when the two protrusions of the cylindrical portion are engaged with the screw of the lock adapter of the male syringe.

13. The syringe kit according to claim 12, wherein the abutment portion is continuous from each proximal end of the two protrusions to a position separated by at least 4 mm toward the female barrel body from a distal end of the cylindrical portion.

14. A syringe connection method for connecting the male syringe and the female syringe of the syringe kit of claim 1 by screwing, the syringe connection method comprising:

causing the two protrusions having the inclined surface to advance over the screw thread of the lock adapter by the torque smaller than the torque at which the female syringe breaks when the female syringe is engaged with the convex reference conical fitting for the stress crack test specified in ISO 594-2 when screwing the screw and the two protrusions and generating a click feeling along with the advancement.

15. The syringe connection method according to claim 14, wherein the cylindrical portion has an abutment portion provided at a position closer to a proximal end than the two protrusions on the outer circumferential surface of the cylindrical portion, the method comprising:
suppressing an inclination of an axis of the cylindrical portion with respect to an axis of the lock adapter when the screw and the two protrusions are engaged with the abutment portion abutting on the inner circumferential surface of the lock adapter.

16. The syringe connection method according to claim 14, further comprising:
molding both the male syringe barrel and the female syringe barrel from a cyclic polyolefin.

17. A syringe kit comprising:
a male syringe having a male syringe barrel that includes a nozzle configured as a male luer, a lock adapter which surrounds an outer circumferential surface of the nozzle and has a screw on an inner circumferential surface, and a male barrel body connected to the nozzle and the lock adapter;
a female syringe having a female syringe barrel that includes a cylindrical portion configured as a female luer to which the nozzle is connectable, two protrusions which protrude from an outer circumferential surface of the cylindrical portion and are engageable with the screw of the lock adapter, and a female barrel body connected to the cylindrical portion, each of the two protrusions has an inclined surface;
when the screw and the two protrusions are engaged, the two protrusions which each have the inclined surface are configured to advance over a screw thread of the lock adapter; and
wherein the two protrusions each have a chamfered corner chamfered on a side opposing the inclined surface, and the chamfered corner is an arcuate curved surface.

18. The syringe kit according to claim 17, wherein the inclined surface of each of the two protrusions is configured to oppose a trailing flank of the screw of the lock adapter when the two protrusions are engaged with the screw of the lock adapter.

* * * * *